US010909414B2

(12) United States Patent
Frank et al.

(10) Patent No.: US 10,909,414 B2
(45) Date of Patent: Feb. 2, 2021

(54) ENTROPY FIELD DECOMPOSITION FOR IMAGE ANALYSIS

(71) Applicant: THE REGENTS OF THE UNIVERSITY OF CALIFORNIA, Oakland, CA (US)

(72) Inventors: Lawrence R. Frank, San Diego, CA (US); Vitaly L. Galinsky, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 355 days.

(21) Appl. No.: 15/570,603

(22) PCT Filed: May 2, 2016

(86) PCT No.: PCT/US2016/030446
§ 371 (c)(1),
(2) Date: Oct. 30, 2017

(87) PCT Pub. No.: WO2016/176684
PCT Pub. Date: Nov. 3, 2016

(65) Prior Publication Data
US 2018/0285687 A1    Oct. 4, 2018

Related U.S. Application Data

(60) Provisional application No. 62/155,404, filed on Apr. 30, 2015.

(51) Int. Cl.
*G06K 9/60* (2006.01)
*G06K 9/62* (2006.01)
(Continued)

(52) U.S. Cl.
CPC .............. *G06K 9/6214* (2013.01); *A61B 5/00* (2013.01); *A61B 5/055* (2013.01);
(Continued)

(58) Field of Classification Search
CPC ............ G06K 9/6214; G06K 9/00536; G06K 9/6247; G06K 9/6271; A61B 5/00;
(Continued)

(56) References Cited

U.S. PATENT DOCUMENTS 6,992,484 B2   1/2006  Frank
7,672,790 B2   3/2010  McGraw et al.
(Continued)

FOREIGN PATENT DOCUMENTS

WO    2014144331 A1    9/2014

OTHER PUBLICATIONS

Galinsky et al. (Simultaneous Multi-scale Diffusion Estimation and Tractography Guided by entropy Spectrum Pathways) (Year: 2015).*
(Continued)

*Primary Examiner* — Solomon G Bezuayehu
(74) *Attorney, Agent, or Firm* — Eleanor Musick; Musick Davison LLP

(57) ABSTRACT

A system and method for analysis of complex spatio-temporal data utilize complimentary general approaches to data analysis: information field theory (IFT), which reformulates Bayesian theory in terms of field theory in order to incorporate the important and often overlooked conditions that ensure continuity of underlying parameter spaces that are to be estimated from discrete data, and entropy spectrum pathways (ESP), which uses the principle of maximum entropy to incorporate prior information on the structure of the underlying space in order to estimate measures of connectivity.

10 Claims, 17 Drawing Sheets

(51) Int. Cl.
| | |
|---|---|
| *A61B 5/00* | (2006.01) |
| *A61B 5/055* | (2006.01) |
| *G01R 33/56* | (2006.01) |
| *G06T 7/00* | (2017.01) |
| *G06K 9/00* | (2006.01) |
| *G01R 33/48* | (2006.01) |
| *G01R 33/563* | (2006.01) |

(52) U.S. Cl.
CPC ..... *G01R 33/5608* (2013.01); *G06K 9/00536* (2013.01); *G06K 9/6247* (2013.01); *G06K 9/6271* (2013.01); *G06T 7/0012* (2013.01); *G01R 33/4806* (2013.01); *G01R 33/56341* (2013.01); *G06T 7/0016* (2013.01); *G06T 2207/10044* (2013.01); *G06T 2207/10081* (2013.01); *G06T 2207/10088* (2013.01); *G06T 2207/20048* (2013.01); *G06T 2207/30016* (2013.01)

(58) Field of Classification Search
CPC ............... A61B 5/055; G01R 33/5608; G01R 33/4806; G01R 33/56341; G06T 7/0012; G06T 2207/10088
See application file for complete search history.

(56) References Cited

U.S. PATENT DOCUMENTS

| | | | |
|---|---|---|---|
| 7,773,074 | B2 | 8/2010 | Arenson et al. |
| 8,742,754 | B2 | 6/2014 | Hasan |
| 9,404,986 | B2 | 8/2016 | White et al. |
| 9,645,212 | B2 | 5/2017 | Frank et al. |
| 2005/0119834 | A1 | 6/2005 | Kita et al. |
| 2005/0154701 | A1 | 7/2005 | Parunak et al. |
| 2005/0213809 | A1 | 9/2005 | Lees et al. |
| 2006/0259282 | A1 | 11/2006 | Failla et al. |
| 2007/0087756 | A1 | 4/2007 | Hoffberg |
| 2008/0091388 | A1 | 4/2008 | Failla et al. |
| 2008/0287796 | A1 | 11/2008 | Kiraly et al. |
| 2011/0201935 | A1 | 8/2011 | Collet-Billon et al. |
| 2011/0255763 | A1 | 10/2011 | Bogoni et al. |
| 2011/0297369 | A1 | 12/2011 | Kumaran et al. |
| 2014/0249787 | A1* | 9/2014 | Orozco Lopez ........ G16B 15/00 703/2 |
| 2016/0004972 | A1* | 1/2016 | Alboszta ................. G06N 7/005 706/52 |
| 2016/0011335 | A1* | 1/2016 | Sasaki ..................... G01W 1/10 702/3 |
| 2016/0110911 | A1* | 4/2016 | Frank ................... A61B 5/0042 382/131 |
| 2016/0210742 | A1 | 7/2016 | Weiss |
| 2016/0225146 | A1 | 8/2016 | Frank et al. |

OTHER PUBLICATIONS

Balmforth et al. (Pattern Formation in Hamiltonian systems with continuous spectra; a normal-form single-wave model) (Year: 2013).*
Balmforth, N. J. et al. "Pattern formation in Hamiltonian systems with continuous spectra; a normal-form single-wave model." In: arXiv preprint arXiv:1303.0065. Mar. 1, 2013 from https://arxiv.org/pdf/1303.0065.pdf downloaded on Aug. 10, 2016, 56 pgs.
Behrens, T.E.J. et al., Probabilistic diffusion tractography with multiple fibre orientations: What can we gain?; NeuroImage vol. 34 (2007) pp. 144-155.
Bista, Sujal et al., Visualization of Brain Microstructure through Spherical Harmonics Illumination of High Fidelity Spatio-Angular Fields; IEEE Trans Vis Comput Graph, Dec. 2014; 20(12) : 2416-2525.
Burda, Z. et al., The various facets of random walk entropy, presented at the 22nd Marian Smoluchowski Symposium on Statistical Physics, Zakopane, Poland, Sep. 12-17, 2009, 40 pages.
Campbell, Jennifer S.W. et al., Diffusion Imaging of White Matter Fibre Tracts, Thesis submitted to McGill University, Nov. 8, 2004, Montreal, Canada, © Jennifer Campbell, 2004, 183 pages.
Hang, Ping et al., "Predictability of Linear Coupled Systems. Part I: Theoretical Analyses" Journal of Climate, vol. 17, Apr. 2004, p. 1474-1486.
Chung, Moo K. et al., Encoding cortical surface by spherical harmonics, Statistica Sinica vol. 18 (2008), 1269-1291.
Descoteaux, Maxime et al., Deterministic and probabilistic Q-Ball tractography: from diffusion to sharp fiber distributions, No. 6273, Aug. 2007, Theme Bio, 36 pages.
Enrvik, Aron, 3D visualization of weather radar data, Thesis project in computer graphics at Linkoping University, Linkoping, Jan. 2002, LITH-ISY-EX-3252-2002, 92 pgs.
Frank, Lawrence R. et al., Information pathways in a discorded lattice, Physical Review, E 89, 032142 (2014), 11 pgs.
Galinsky, Vitaly L. et al. "Simultaneous Multi-Scale Diffusion Estimation and Tractography Guided by Entropy Spectrum Pathways," IEEE Transactions on Medical Imaging, vol. 34, Issue 5, Dec. 18, 2014, 1177-1193.
Galinsky, Vitaly L. et al., Automated segmentation and shape characterization of volumetric data, NeuroImage vol. 92 (2014) pp. 156-168.
Galinsky, Vitaly L. et al., Simultaneous multi-scale diffusion estimation and tractography guided by entropy spectrum pathways, IEEE Transactions on Medical Imaging, Dec. 2104, vol. 34, Issue 5, pp. 1177-1193.
Soncalves, Vitor, Interaction and visualization techniques for volumetric data of various scalar modalities: Integration of visualization and interaction, Electronica E. Telecomunicacoes, vol. 5, No. 3, Jun. 2011, pp. 344-351.
Huang, Heng et al., Functional analysis of cardiac MR images using SPHARM modeling, Proc. SPIE 5747, Medical Imaging 2005: Image Processing, May 5, 2005, 1384; doi:10.1117/12.595954.
Le Bihan, Denis, Diffusion, confusion and functional MRI, NeuroImage xxx, 2011, doi:10.1016/j.neuroimage.2011.09.058, 6 pages.
Lu, Meng et al. Snake-based brain white matter fiber reconstruction, Bio-Medical Materials and Engineering vol. 24 (2014) pp. 2945-2953.
Mukherjee, P. et al., Diffusion tensor MR imaging and fiber tractography: technical considerations, AJNR Am J. Neuroradiol vol. 29, May 2008, pp. 843-852.
Mukherjee, P. et al., Diffusion tensor MR imaging and fiber tractography: theoretic underpinnings, AJNR Am J. Neuroradiol vol. 29, Apr. 2008, pp. 632-641.
PCT/US2016/030445, International Search Report dated Aug. 8, 2016, 3 pages.
PCT/US2016/030446, Written Opinion dated Aug. 8, 2016, 12 pages.
Peters, J.F. et al., Classification of meteorological volumetric radar data using rough set methods, Pattern Recognition Letters, vol. 24 (2003) pp. 911-920.
Scholköpf, Bernhard et al., Nonlinear Component Analysis as a Kernel Eigenvalue Problem, Neural Computation, vol. 10, Jul. 1, 1998, pp. 1299-1319.
Senjem, Matthew L. et al., Comparison of different methodological implementations of Voxel-based morphometry in neurodegenerative disease, Neuroimage vol. 26(2), Jun. 2005, pp. 600-608.
Shaw, Christopher D. et al., Real-time weather data on terrain, Proc. SPIE 4368, Visualization of Temporal and Spatial Data for Civilian and Defense Applications, Aug. 23, 2001, 8 pages.
Sinatra, Roberta et al., Maximal-entropy random walks in complex networks with limited information, Physical Review, vol. 83, 030103(R), 2011, 4 pages.
Styner, Martin, et al., Statistical shape analysis of brain structures using SPHARM-PDM, Insight Journal, MICCAI 2006 Opensource Workshop, 7 pgs.
Tournier, Jacques-Donald et al., Diffusion tensor imaging and beyond, Magn Reson Med. vol. 65(6), Jun. 2011, pp. 1532-1556.

* cited by examiner

ENTROPY FIELD DECOMPOSITION FOR IMAGE ANALYSIS

RELATED APPLICATIONS

This application is a 371 national stage filing of International Application No. PCT/US2016/030446, filed May 2, 2016, which claims the benefit of U.S. Provisional Application No. 62/155,404, filed Apr. 30, 2015, each of which is incorporated herein by reference in its entirety.

GOVERNMENT RIGHTS

This invention was made with government support under Grant R01MH096100 awarded by the National Institutes of Health and Grant DBI-1147260 awarded by the National Science Foundation. The government has certain rights in the invention.

FIELD OF THE INVENTION

The invention relates to a method for analyzing images comprising spatio-temporal data and more specifically to a method for analysis of data generated using imaging techniques to detect and predict patterns within complex physical systems.

BACKGROUND

Humans obtain the vast majority of sensory input through their visual system. Significant effort has been made to artificially enhance this sense. The limitations of the human visual system have been greatly expanded through the development of novel instrumentation capable of detecting other spectra, e.g., infrared, ultraviolet, X-ray, radio wave, microwave, etc., and computer algorithms for generating images from the data gathered by such instrumentation. Challenges in extracting useful knowledge from this data are ubiquitous in the sciences, ranging from extracting a signal from a noisy environment to development of predictive models of complex systems based on huge volumes of multivariate data.

In a wide range of scientific disciplines, experimenters are faced with the problem of discerning spatial-temporal patterns in data acquired from exceedingly complex physical systems in order to characterize the structure and dynamics of the observed system. Such is the case in the two fields of research that involve complex behavior: functional magnetic resonance imaging (FMRI) and mobile Doppler radar (MDR). The multiple time-resolved volumes of data acquired in these methods are from exceedingly complex and non-linear systems: the human brain and severe thunder storms. Furthermore, the instrumentation in both of these fields continues to improve dramatically, facilitating increasingly more detailed data of spatial-temporal fluctuations of the working brain and of complex organized coherent storm scale structures such as tornadoes.

MRI scanners are now capable of obtaining sub-second time resolved whole brain volumes sensitive to temporal fluctuations in activity with highly localized brain regions identified with specific modes of brain activity, such as activity in the insula, which is associated with the so-called "executive control network" of the brain. In functional MRI (fMRI), the data are 4-dimensional, composed of temporal variations in the signal from a volumetric imaging operation. The data consist of large volumes of densely sampled, relatively low signal-to-noise, voxels acquired at many time points, presenting a significant challenge due to the multitude of spatial and temporal scales and potential combinations of interactions.

Magnetic Resonance Imaging (MRI), or nuclear magnetic resonance imaging, is commonly used to visualize detailed internal structures in the body. MRI provides superior contrast between the different soft tissues of the body when compared to x-ray computed tomography (CT). Unlike CT, MRI involves no ionizing radiation because it uses a powerful magnetic field to align protons, most commonly those of the hydrogen atoms of the water present in tissue. A radio frequency electromagnetic field is then briefly turned on, causing the protons to alter their alignment relative to the field. When this field is turned off the protons return to their original magnetization alignment. These alignment changes create signals which are detected by a scanner. Images can be created because the protons in different tissues return to their equilibrium state at different rates. By altering the parameters on the scanner this effect is used to create contrast between different types of body tissue. MRI may be used to image every part of the body, and is particularly useful for neurological conditions, for disorders of the muscles and joints, for evaluating tumors, and for showing abnormalities in the heart and blood vessels. Magnetic resonance imaging (MRI) methods provide several tissue contrast mechanisms that can be used to assess the micro- and macrostructure of living tissue in both health and disease. Diffusion MRI is a method that produces in vivo images of biological tissues weighted with the local microstructural characteristics of water diffusion. There are two distinct forms of diffusion MRI, diffusion weighted MRI and diffusion tensor MRI.

In diffusion weighted imaging (DWI), each image voxel (three-dimensional pixel) has an image intensity that reflects a single best measurement of the rate of water diffusion at that location. This measurement is more sensitive to early changes such as occur after a stroke compared to traditional MRI measurements such as T1 or T2 relaxation rates. DWI is most applicable when the tissue of interest is dominated by isotropic water movement, e.g., grey matter in the cerebral cortex and major brain nuclei—where the diffusion rate appears to be the same when measured along any axis. Traditionally, in diffusion-weighted imaging (DWI), three gradient-directions are applied, sufficient to estimate the trace of the diffusion tensor or "average diffusivity", a putative measure of edema. Clinically, trace-weighted images have proven to be very useful to diagnose vascular strokes in the brain, by early detection (within a couple of minutes) of the hypoxic edema.

Diffusion tensor imaging (DTI) is a technique that enables the measurement of the restricted diffusion of water in tissue in order to produce neural tract images instead of using this data solely for the purpose of assigning contrast or colors to pixels in a cross sectional image. It also provides useful structural information about muscle—including heart muscle, as well as other tissues such as the prostate. DTI is important when a tissue—such as the neural axons of white matter in the brain or muscle fibers in the heart—has an internal fibrous structure analogous to the anisotropy of some crystals. Water tends to diffuse more rapidly in the direction aligned with the internal structure, and more slowly as it moves transverse to the preferred direction. This also means that the measured rate of diffusion will differ depending on the position of the observer. In DTI, each voxel can have one or more pairs of parameters: a rate of diffusion and a preferred direction of diffusion, described in terms of three dimensional space, for which that parameter is valid. The properties of each voxel of a single DTI image may be calculated by vector or tensor math from six or more different diffusion weighted acquisitions, each obtained with a different orientation of the diffusion sensitizing gradients. In some methods, hundreds of measurements—each making up a complete image—can be used to generate a single resulting calculated image data set. The higher information content of a DTI voxel makes it extremely sensitive to subtle pathology in the brain. In addition, the directional information can be exploited at a higher level of structure to select and follow neural tracts through the brain—a process called "tractography."

More extended diffusion tensor imaging (DTI) scans derive neural tract directional information from the data using 3D or multidimensional vector algorithms based on three, six, or more gradient directions, sufficient to compute the diffusion tensor. The diffusion model is a rather simple model of the diffusion process, assuming homogeneity and linearity of the diffusion within each image voxel. From the diffusion tensor, diffusion anisotropy measures such as the fractional anisotropy (FA) can be computed. The principal direction of the diffusion tensor can be used to infer the white-matter connectivity of the brain. Recently, more advanced models of the diffusion process have been proposed to overcome the weaknesses of the diffusion tensor model. Amongst others, these include q-space imaging and generalized diffusion tensor imaging.

Functional magnetic resonance imaging (fMRI) has revolutionized neuroscience research by providing a method to non-invasively observe spatial and temporal variations in brain activity. The initial and still dominant fMRI approach is to measure changes in the blood oxygenation level dependent (BOLD) signal in response to well controlled input stimuli designed to probe specific brain systems. This is the so-called "task-based" fMRI. More recently, however, as significant advances in MRI scanner technologies have facilitated the acquisition of high spatial and temporal resolution whole brain fMRI data, an increasing number of studies have returned to the study of brain activity in the absence of external stimulation, the so-called "resting state" condition. In resting state fMRI (rs-fMRI), one seeks to identify synchronous fluctuations in the BOLD signal that characterize "modes" of brain activity. However, the reconstruction of brain networks from these signal fluctuations poses a significant challenge because they are generally non-linear, non-Gaussian, and can overlap in both their spatial and temporal extent. Thus, these rs-fMRI data present a unique and significant analysis challenge that has yet to be adequately solved, and thus severely limits the utility of the method. The existence of an input stimuli in task-based fMRI implementations provides a reference against which to assess signal changes and facilitates the application of the vast array of analysis methods available for signal detection and parameter estimation. Resting state fMRI data, on the other hand, has no such input, and thus there is a fundamental problem of defining the question to be asked of the data. Brain activity as observed by rs-fMRI is generally characterized by spatially and temporally coherent signal changes that reflect "modes" of brain function. These changes can occur on multiple spatial and temporal scales. A variety of techniques have been devised to address this problem, however, the predominant approaches are based on the presupposition of the statistical properties of complex brain signal parameters, which are unprovable but facilitate the analysis.

A completely different application of spatio-temporal data analysis is the analysis of Doppler radar data, which has implications in the tracking and potential prediction of severe weather events such as tornadoes. Mobile dual Doppler systems can resolve wind velocity and reflectivity within a tornadic supercell with temporal resolution of just a few minutes and observe highly localized dynamical features such as secondary rear flank downdrafts. Current methods of severe weather detection rely almost entirely on visual and subjective interpretation of Doppler radar data.

These are just a few examples of the many physical systems of interest to scientists that are highly non-linear and non-Gaussian, and in which detecting, characterizing, and quantitating the observed patterns and relating them to the system dynamics poses a significant data analysis challenge.

BRIEF SUMMARY OF THE INVENTION

According to embodiments of the invention, a system and method are provided for the analysis of spatiotemporal signal fluctuations in time-resolved noisy volumetric data acquired from non-linear and non-Gaussian systems. The inventive system and method utilize complimentary general approaches to data analysis: information field theory (IFT), which reformulates Bayesian theory in terms of field theory in order to incorporate the important and often overlooked conditions that ensure continuity of underlying parameter spaces that are to be estimated from discrete data, and entropy spectrum pathways (ESP), which uses the principle of maximum entropy to incorporate prior information on the structure of the underlying space in order to estimate measures of connectivity. ESP is described in U.S. Patent Publication No. 2016/0110911, which is incorporated herein by reference. Both methods incorporate Bayesian theory, thus using prior information to uncover underlying structure of the unknown signal. Unification of ESP and IFT creates an approach that is non-Gaussian and non-linear by construction and is found to produce unique spatio-temporal modes of signal behavior that can be ranked according to their significance, from which space-time trajectories of parameter variations can be constructed and quantified. This method resulting from the combination of ESP and IFT is called "entropy field decomposition" or "EFD", and it provides a quantitative theory for the estimation of complicated coherent spatial-temporal signal structures in the absence of a signal model. A key feature of the EFD theory is that it does not assume either that the signal or noise is Gaussian or that the parameter relationships are linear.

The disclosed method and system are applicable to numerous problems of analysis of complex physical systems. The present disclosure provides examples of real world applications of the theory to the analysis of data bearing completely different, unrelated nature, lacking any underlying similarity. In one illustrative embodiment, the EFD method may be used for analysis of resting state functional magnetic resonance imaging (rsFMRI) data, providing an efficient and accurate computational method for assessing and categorizing brain activity. In another embodiment, the EFD method is applied to the analysis of a strong atmospheric storm circulation system during the complicated stage of tornado development and formation using data recorded by a mobile Doppler radar system.

In one implementation, a method is provided for analyzing spatio-temporal Doppler radar data for the purpose of detecting severe weather events, such as tornadoes. The method provides robust and quantitative measures of dynamic variations in severe weather parameters, such as maximum reflectivity, tilt, stretch, and vorticity, as well as extended field variables such as vortex lines, all of which play a key role in the generation and propagation of severe weather events such as tornados, and as such is important not only in helping aid researchers in better understanding the mechanisms of severe weather generations (e.g., tornadogenesis) but provides a rapid and robust method for severe weather detection that can be used to enhance detection systems for public safety.

The invention provides an automated detection system based upon a novel method of entropy field decomposition (EFD), which combines the structure analysis techniques disclosed in International Application NO. PCT/US2014/055712 (Publ. No. WO 2015/039054 A1) (which is incorporated herein by reference), entropy spectrum pathways ("ESP"), and geometrical optics guided entropy spectrum pathways tractography ("GO-ESP", U.S. Patent Publication No. 2016/0110911). In an illustrative example, the method is able to quantitate spatio-temporal patterns and correlations of tensor variables and is, thus, sensitive to severe weather features not readily visible to the naked eye, making it not only more automated, but more quantitative, than existing methods. Another potential application of the inventive method is to medical imaging systems, such as FMRI.

Also provided is a method for plant phenotyping based on root structure analysis derived from diffusion tensor magnetic resonance imaging (DT-MRI). The method provides a non-invasive quantitation of root architecture including basic parameters such as depth and maximum angular extent, but also additional characterization in terms of angular distributions and network properties. The method is non-invasive and thus can be used in longitudinal studies without disrupting the plant system. This capability has important implications for the design of plant phenotypes that are robust even in drought stricken environments and thus has potentially profound implications for food security on a global scale.

In one aspect, a method for analysis of complex spatio-temporal data, comprises, using a computer processor for: receiving image data from an image detector, wherein the image data comprises points within a lattice; ranking a plurality of optimal paths within the lattice according to path entropy, wherein the rankings are arranged in a coupling matrix; using eigenvalues and eigenvectors from the coupling matrix to construct an information Hamiltonian; determining mode amplitudes corresponding to spatially and temporally interacting modes of the information Hamiltonian; and generating an output comprising a display of the mode amplitudes. In some embodiments, the information Hamiltonian is of the form $$H(d, a_k) = -j_k^\dagger a_k + \frac{1}{2}a_k^\dagger \Lambda a_k + \sum_{n=1}^{\infty} \frac{1}{n!}\sum_{k_1}^{K} \ldots \sum_{k_n}^{K} \tilde{\Lambda}_{k_1 \ldots k_n}^{(n)} a_{k_1} \ldots a_{k_n},$$

where matrix $\Lambda$ is the diagonal matrix $\text{Diag}\{\lambda_1, \ldots, \lambda_K\}$ composed of eigenvalues of a noise corrected coupling matrix, $a_k$ is an amplitude of the kth mode, and $j_k$ is the amplitude of the kth mode in the expansion of the source j. In certain embodiments the mode amplitudes are determined according to the relationship $$\Lambda a_k = \left( j_k - \sum_{n=1}^{\infty} \frac{1}{n!}\sum_{k_1}^{K} \ldots \sum_{k_n}^{K} \tilde{\Lambda}_{kk_1 \ldots k_n}^{(n+1)} a_{k_1} \ldots a_{k_n} \right).$$

In some implementations, the image detector is a magnetic resonance imaging system and the complex spatio-temporal data comprises functional magnetic resonance image (FMRI) data, and wherein the mode amplitudes correspond to functional tractography and functional eigentracts. In other implementations, the image detector is a Doppler radar system and the complex spatio-temporal data comprises Doppler radar data, and wherein the mode amplitudes correspond to tilt, stretch and vorticity.

In another aspect, a method for analysis of complex spatio-temporal data comprises receiving in a computer processor image data from an image detector, wherein the image data comprises a plurality of voxels; and causing the computer processor to perform the steps of: generating a coupling matrix by ranking optimal paths between voxels according to path entropy; determining entropy spectrum pathway (ESP) eigenvalues and eigenvectors for the coupling matrix; constructing an information Hamiltonian using the ESP eigenvalues and eigenvectors, wherein the information Hamiltonian includes a diagonal matrix of ESP eigenvalues and interaction terms constructed with the ESP eigenvalues and eigenvectors; estimating mode amplitudes corresponding to spatially and temporally interacting modes of the information Hamiltonian; and generating an output comprising a display of the mode amplitudes. In some embodiments, the image detector may be a magnetic resonance imaging system and the complex spatio-temporal data comprises functional magnetic resonance image (FMRI) data, wherein the mode amplitudes correspond to functional tractography and functional eigentracts. In other embodiments, the image detector may be a Doppler radar system and the complex spatio-temporal data comprises Doppler radar data, wherein the mode amplitudes correspond to tilt, stretch and vorticity.

In yet another aspect, a method for analysis of complex multivariate spatio-temporal data, includes receiving in a computer processor image data from an image detector, wherein the image data comprises a plurality of voxels; and causing the computer processor to perform the steps of: ranking pathways between voxels according to path entropy and generating a coupling matrix therefrom; determining eigenvalues and eigenvectors for the coupling matrix; constructing an information Hamiltonian using eigenvalues and eigenvectors; determining mode amplitudes corresponding to spatially and temporally interacting modes of the information Hamiltonian; and generating an output comprising a display of the mode amplitudes. In certain embodiments, the image detector is a magnetic resonance imaging system and the complex spatio-temporal data comprises functional magnetic resonance image (FMRI) data, and the mode amplitudes correspond to functional tractography and functional eigentracts. In other embodiments, the image detector is a Doppler radar system and the complex spatio-temporal data comprises Doppler radar data, and the mode amplitudes correspond to tilt, stretch and vorticity.

In still another aspect, a method for analysis of complex spatio-temporal data, includes receiving in a computer processor image data from an image detector, wherein the image data comprises a plurality of voxels; and causing the computer processor to perform the steps of: generating a plurality of temporal pair correlation functions for every nearest neighbor voxel in a vicinity of each voxel; computing a correlation value for each pair of voxels; computing a spatial eigenmode with zero frequency using each correlation value as a coupling coefficient from a propagator; calculating eigenmodes for each frequency using the zero frequency spatial eigenmode; generating interaction patterns by summation of input from terms resulting from orders of correlation between the eigenmodes and a residual signal; and generating an output comprising a display of the interaction patterns. In some embodiments, the image detector is a magnetic resonance imaging system, and the interaction patterns correspond to functional tractography and functional eigentracts. In other embodiments, the image detector is a Doppler radar system, and the interaction patterns correspond to tilt, stretch and vorticity.

In still another aspect, a non-transitory computer readable medium has instructions stored therein which, when executed by a computer processor, cause the computer processor to: receive data from an imaging instrumentation, the data comprising space-time volumetric data detected within a system; identify patterns in the data using EFD analysis; and generate an output comprising a quantitative representation of the system. In some embodiments, the imaging instrumentation is a magnetic resonance imaging system, and the quantitative representation corresponds to functional tractography and functional eigentracts. In another implementation, the image detector is a Doppler radar system, and the quantitative representation corresponds to tilt, stretch and vorticity.

In yet another aspect, a method for analysis of complex spatio-temporal data extracted from an image comprising a plurality of spatial positions and a plurality of fields, at least a portion of which are interacting, includes using a computing device to determine values of mean field at every spatial position; determine spatio-temporal eigenmodes in spatial-frequency space assuming non-interacting fields; determine interactions between the eigenmodes; and generate an output comprising space/time localization patterns that correspond to modes of the data. In certain implementations, the image is generated by a magnetic resonance imaging system and the complex spatio-temporal data comprises functional magnetic resonance image (FMRI) data, where the space/time localization patterns correspond to functional tractography and functional eigentracts. In other implementations, the image is generated by a Doppler radar system and the complex spatio-temporal data comprises Doppler radar data, where the space/time localization patterns correspond to tilt, stretch and vorticity.

The inventive method is based upon techniques for characterization of behavior within complex data. This method may be used for a wide range of applications in which connectivity needs to be inferred from complex multidimensional data, such as magnetic resonance imaging (MRI) of the human brain using diffusion tensor magnetic resonance imaging for characterization of neuronal fibers and brain connectivity, or in the analysis of networks in the human brain using functional MRI.

Unification of ESP and IFT creates an approach that is non-Gaussian and non-linear by construction to produce unique spatio-temporal modes of signal behavior that can be ranked according to their significance, from which space-time trajectories of parameter variations can be constructed and quantified.

BRIEF DESCRIPTION OF THE DRAWINGS

FIG. 6C shows the restored time signals. FIG. 6D shows the original noisy signal with the restored signals superimposed.

DETAILED DESCRIPTION OF EXEMPLARY EMBODIMENTS

Figure 1:
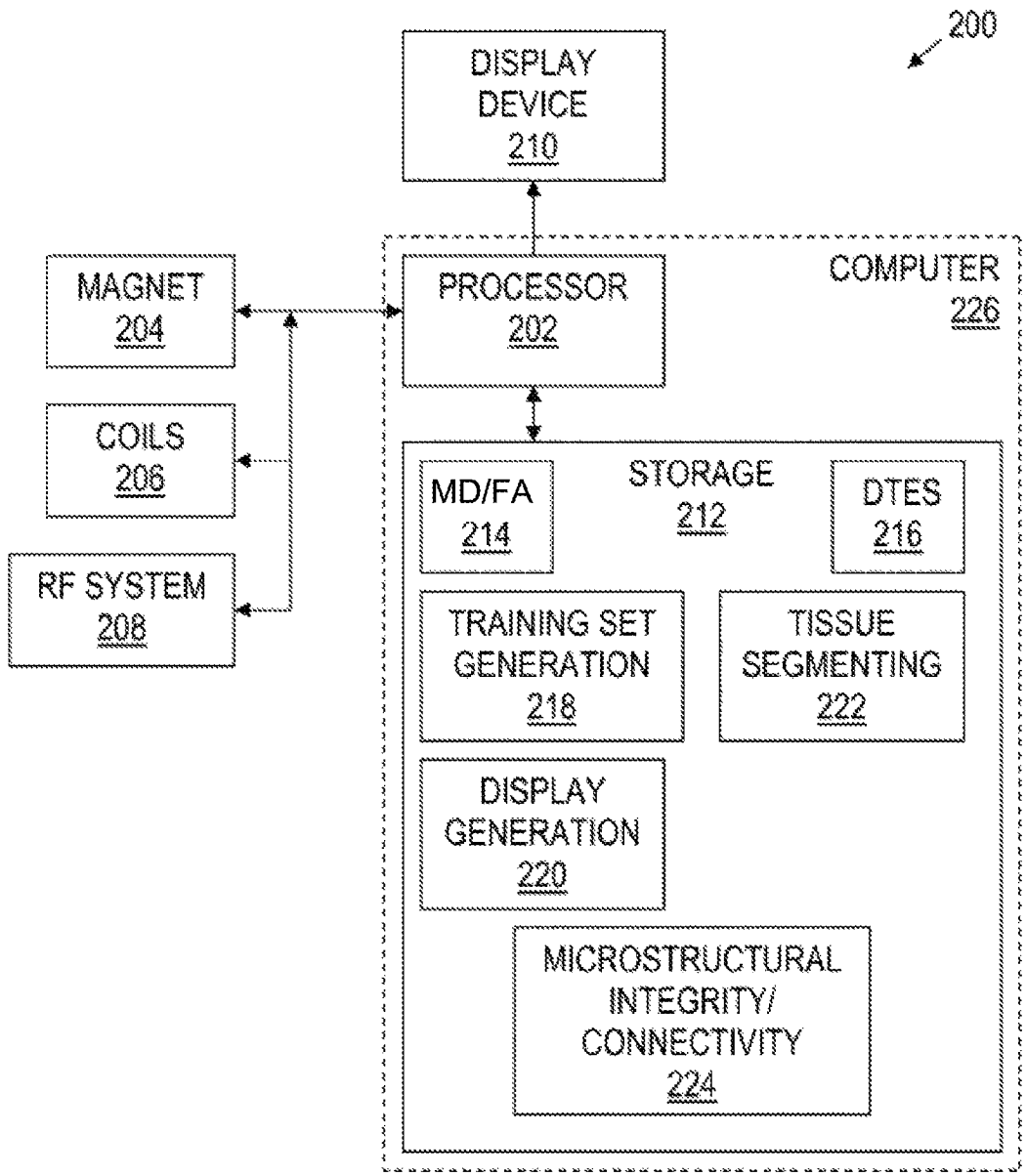
FIG. 1 is a block diagram of an exemplary medical imaging system in accordance with various embodiments.

Entropy field decomposition (EFD) is a method that combines the prior local coupling information obtained using entropy spectrum pathway (ESP) techniques, which are disclosed in U.S. Patent Publication No. US2016/0110911, published Apr. 21, 2016 (incorporated herein by reference), with information field theory (IFT) to provide for the efficient characterization and ranking of global information pathways in complex multivariate spatio-temporal data.

Applications of the EFD method include any commercial neuroscience application involved in the quantification of connectivity, including neural fiber connectivity using diffusion tensor imaging, functional connectivity using functional MRI, or anatomical connectivity using segmentation analysis. The EFD method may also be used as a tool for characterization of connectivity in networks, examples of which include the internet and communications systems. Additional applications of EFD can be found in the analysis of information flow in disordered systems, for example, prediction of severe weather. For tornados, spatio-temporal analysis of point patterns and lattice data derived from historical weather records can be used to model tornado behavior. Further, simulations of a tornado's interaction with surrounding objects, such as buildings and vehicles, can be developed using model in which objects in the tornado scene are represented by connected voxels and a corresponding graph storing the link information. (See, e.g., S. Liu, et al., "Real time simulation of a tornado", *Visual Computer*, 23(8):559-567, May 10, 2007).

Specific examples described herein are directed to the use of EFD for diffusion tensor imaging of neural pathways, tornadogenesis, and root structural analysis. Such data are currently evaluated by human visual interpretation. In each case, the EFD method is able to quantitate spatio-temporal patterns and correlations of tensor variables, making it more sensitive to subtle features not readily visible to the naked eye, making it not only more automated, but more quantitative, than existing methods.

As will be readily apparent to those of skill in the art, many other fields will also benefit from the improved ability to analyze complex spatio-temporal data provided by the EFD method, including, but not limited to, environment and climate, medical imaging, public health and safety, transportation, and mobile commerce. Accordingly, the subject matter described in the examples is intended to be illustrative, and not limiting, of the EFD method disclosed herein.

Entropy Spectrum Pathways: Briefly, the method referred to as "Entropy Spectrum Pathways", or "ESP", is based on the description of pathways according to their entropy, and provides a tool for ranking the significance of the pathways. The method is a generalization of the maximum entropy random walk ("MERW"), which appears in the literature as a description of a diffusion process that possesses localization of probabilities. ESP expands the use of MERW beyond diffusion, and applies it as a measure of information. According to the ESP method, the MERW solution can be viewed as a specific manifestation of a more general result concerning inference on a lattice which has nothing necessarily to do with diffusion, or any other physical process. The general approach results in a theoretical framework suitable for application to a wide range of problems involved with analysis of disordered lattice systems. Further description of ESP is provided below.

Information Field Theory: Consider the case where the data $\{d_{i,j}\}$ consist of n measurements in time $t_i$, $=1, \ldots, n$ at N spatial locations $x_j$, $j=1, \ldots, N$ (or equivalently $\{d_l\}$, where $\xi_l$, $l=1, \ldots nN$ defines a set of space-time locations). The spatial locations are assumed to be arranged on a Cartesian grid and the sampling times are assumed to be equally spaced. Neither of these is required in what follows, but merely simplify and clarify the analysis. For most applications we are interested in, the data d are assumed to be 4-dimensional, composed of temporal variations in the signal from a volumetric (three spatial dimensions) imaging experiment. Each data point is of the form $$d_{i,j} = \hat{R} s_{i,j} + e_{i,j} \quad (1)$$

where $\hat{R}$ is an operator that represents the response of the measurement system to a signal $s_{i,j}$, and $e_{i,j}$ is the noise with the covariance matrix $\Sigma_e = ee^\dagger$) where † means the complex conjugate transpose.

From the Bayesian viewpoint, the goal is to estimate the unknown signal from the peak in the joint posterior probability, given the data d and any available prior information I. The posterior distribution can be written via Bayes theorem, as $$\underbrace{p(s|d, I)}_{\text{Posterior}} = \frac{\overbrace{p(d, s|I)}^{\text{Joint probability}}}{\underbrace{p(d|I)}_{\text{Evidence}}} = \frac{\overbrace{p(d|s, I)}^{\text{Likelihood}} \overbrace{p(s|I)}^{\text{Prior}}}{p(d|I)} \quad (2)$$

For the case of a known model, the denominator is a constant and the posterior distribution is just the product of the likelihood and the prior distribution. With a non-informative, or "flat" prior, the posterior distribution is just the likelihood, and thus the peak in the posterior distribution is equivalent to the maximum of the likelihood. Thus, maximum likelihood methods implicitly assume: 1) the model is correct; and 2) there is no prior information.

Information field theory re-expresses the probabilistic (or Bayesian) prescription in the language of fi theory. The critical point to be stressed in our interpretation of Eqn. 1 is that, although the data consist of discrete samples in both space and time, the underlying signal $s_l$ is assumed to be continuous in space-time, and thus characterized by a field $\psi(x, t) \equiv \psi(\xi)$ such that $$s_l = \int \psi(\xi) \delta(\xi - \xi_l) d\xi.$$

This characterization is particularly important in the present context because we seek to not only detect, but in effect, define quantitatively, what is meant by "modes" of space-time variations. As we will show, this can be accomplished well within the context of field theory because the general notion of spatio-temporal patterns can be codified as spatio-temporal modes of a self-interacting field.

The IFT formalism proceeds by identifying the terms in Eqn. 2 with the corresponding structures of field theory:

$$H(d,\psi) = -\ln p(d,\psi|I) \quad \text{Hamiltonian} \quad (3a)$$

$$p(d|I) = \int d\psi e^{-H(d,\psi)} = Z(d) \quad \text{Partition function} \quad (3b)$$

so that the Bayes Theorem providing the posterior distribution Eqn. 2 becomes $$p(\psi|d, I) = \frac{e^{-H(d,\psi)}}{Z(d)} \quad (4)$$

Applied to a signal of the form of Eqn. 1, the information Hamiltonian can be written $$H(d,\psi) = H_0 - h^\dagger \psi + \tfrac{1}{2} \psi^\dagger D^{-1} \psi + H_i(d,\psi), \quad (5)$$

where $H_0$ is essentially a normalizing constant that can be ignored, D is an information propagator, j is an information source, and $H_i$ is an interaction term.

This formulation facilitates the identification of the standard statistical physics result that the partition function (Eqn. 3b) is the moment-generating function from which the correlation functions (also called the "connected components") can be calculated as $$G^c_{ij\ldots m} = \langle s_1 \ldots s_n \rangle_c = \left. \frac{\partial^n \ln Z[j]}{\partial j_i \ldots \partial j_n} \right|_{j=0} \quad (6)$$

with subscript c (for "connected") a standard shorthand for the correlations, (e.g., $\langle a \rangle_c = \langle a \rangle$, $\langle a \, b \rangle_c = \langle a \, b \rangle - \langle a \rangle \langle b \rangle$ and so on for higher correlations, where brackets denote expectation values.) The moments are calculated from an expression identical to Eqn. 6 with ln Z replaced by Z.

If $H_i = 0$, Eqn. 5 describes a free theory, whereas if $H_i \neq 0$, then it describes an interacting theory. The free theory provides only an initial step in the analysis of data that possesses spatio-temporal variations, for it implicitly assumes that the field components do not interact with one another. In most "real life" cases, such as in brain activity or in weather data, one would expect more complex spatio-temporal dynamics in which the modes interact with one another.

Interactions are incorporated into IFT by the inclusion of an interaction Hamiltonian:

$$H_i = \sum_{n=1}^{\infty} \frac{1}{n!} \int \ldots \int \Lambda^{(n)}_{\xi_1 \ldots \xi_n} \psi(\xi_1) \ldots \psi(\xi_n) d\xi_1 \ldots d\xi_n \quad (7)$$

We keep the terms with n=1 and n=2 assuming that they can be regarded as perturbative corrections to the source and the propagator terms. This interaction Hamiltonian includes anharmonic terms resulting from interactions between the eigenmodes of the free Hamiltonian and may be used to describe non-Gaussian signal or noise, a nonlinear response (aka, "mode-mode interaction") or a signal dependent noise (i.e., due to mode-noise interaction).

The classical solution at the minimum of the Hamiltonian ($\delta H/\delta \psi = 0$) is $$\psi(\xi) = D\left( j - \sum_{n=1}^{\infty} \frac{1}{n!} \int \ldots \int \Lambda^{(n+1)}_{\xi \xi_1 \ldots \xi_n} \psi(\xi_1) \ldots \psi(\xi_n) d\xi_1 \ldots d\xi_n \right). \quad (8)$$

To make the connection with standard signal analysis methods, consider the special case where R in Eqn. 1 represents signal model functions F and ψ are the model function amplitudes a and the signal is contaminated by zero mean Gaussian noise with variance $\Sigma_e = \sigma^2$. In the absence of interactions (i.e., the free theory), the expected value of the signal and its covariance (in the Gaussian model, all higher order correlations vanish) then give, from Eqn. 6, the estimates of the amplitudes and their covariances:

$$\langle a \rangle_c = Dj \quad (9)$$

$$\langle a a^\dagger \rangle_c = D \quad (10)$$

where the propagator is then just the noise-weighted covariance of the sampled model functions (sometimes called the "dirty beam")

$$D = \sigma^2 (\hat{F}^\dagger \hat{F})^{-1}, \quad (11)$$

and the source is noise weighted project of the signal onto the sampled model functions (sometimes called the "dirty map"):

$$j = \sigma^{-2} \hat{F}^\dagger d \quad (12)$$

and so the amplitude estimates are, from Eqn. 9, $$\langle a \rangle = F^+ d \quad (13)$$

$$F^+ = (\hat{F}^\dagger \hat{F})^{-1} \hat{F}^\dagger \text{ pseudo-inverse} \quad (14)$$

which is the standard maximum a posterior result that the amplitudes are found from the pseudo-inverse of the model functions times the data. For example, if the signal model functions F are the Fourier basis functions, then the source is the noise weighted Fourier transform of the data while the propagator is the covariance of the sampled Fourier model functions. The rationale for the names "source" and "propagator" becomes clear. The input data $d(t_i)$ projected along the $k^{th}$ component of the model function $F(t_i)$ provides the source of new information, which is then propagated by $(\hat{F}^\dagger \hat{F})_{kl}^{-1}$ from which estimate $\hat{a}_k$ of the $k^{th}$ amplitude is derived.

The solution to Eqn. 13 is found by computing the eigenvectors of the pseudo-inverse $F^+$ and projecting the data d along each of these eigenvectors. The relative contribution of these projections is determined by the eigenvalues associated with each eigenvector. The terminology used to describe this process is that data is being represented in terms of the eigenmodes of the pseudo-inverse.

The purpose of this example is to demonstrate how the general approach relates to standard statistical physics and reduces to well-known results from standard probabilistic methods in the case of very simple signal and noise models. However, we want to emphasize that our interest is in systems with much more complicated signal and noise characteristics. The logical approach remains the same but the identification and description of simple source and propagator terms is no longer possible.

Interaction Hamiltonian by Entropy Spectrum Pathways: The IFT approach outlined in the previous discussion can only be applied to a data analysis problem when (or if) an approximation that describes the nature of the interactions is already known and can be expressed in concise mathematical form. Practically, it means that $\Lambda_{\xi_1 \ldots \xi_n}^{(n)}$ terms in the interaction Hamiltonian Eqn. 7 are known for at least one or several orders of interactions n. In the following discussion, we show how coupling information extracted from the data itself can be used to deduce or constrain the nonlinear an-harmonic terms of the interaction Hamiltonian, thus providing an effective data analysis approach free of usual linearity and Gaussianity assumptions.

The idea that coupling information between different spatio-temporal points can provide powerful prior information has been formalized in the theory of entropy spectrum pathways (ESP), which is based on extension of the maximum entropy random walk (MERW). (See U.S. Patent Publication No. US2016/0110911, incorporated herein by reference.) We will briefly summarize this approach and show how it can be used to obtain nonlinear an-harmonic terms of the interaction Hamiltonian. The power of this concept is that one can generate the path entropy spectrum given any coupling information between neighboring locations, and thus the ESP method can be used to turn coupling information into a quantitative measure of prior information about spatio-temporal configurations.

The concept of locations is a very general one. In the current problem, for example, we will be interested in the paths between two space-time locations $(x_a, t_a) \equiv \xi_a$ and $(x_b, t_b) \equiv \xi_b$ described by a continuous field $\psi(\xi_a)$ and $\psi(\xi_b)$.

The entropy field decomposition (EFD), which is the incorporation of ESP into IFT, is found to produce spatio-temporal modes of signal behavior that can be ranked according to their significance. The EFD can be summarized as follows: (i) Nearest-neighbor coupling information constructed from the data generates, via ESP, correlation structures ranked a priori by probability; (ii) non-Gaussian correlated structures of such shapes are expected in the signal, without the need for a detailed signal model; (iii) a phenomenological interaction information Hamiltonian is constructed from the ESP modes, and the coupling coefficients are computed up to an order determined from the significance of the diff t ESP modes; (iv) this then defines a maximum a posteriori (MAP) a signal estimator specifically constructed to recover the nonlinear coherent structures.

The ESP theory ranks the optimal paths within a disordered lattice according to their path entropy. This is accomplished by constructing a matrix that characterizes the interactions between locations i and j on the lattice called the "coupling matrix":

$$Q_{ij} = e^{-\gamma ij} \quad (15)$$

The $\gamma_{ij}$ are Lagrange multipliers that define the interactions and can be seen as local potentials that depend on some function of the space-time locations $\xi_i$ and $\xi_j$ on the lattice. The eigenvector $\varphi^{(k)}$ associated with the $k^{th}$ eigenvalue $\lambda_k$ of Q $$\sum_j Q_{ij} \phi_j^{(k)} = \lambda_k \phi_i^{(k)} \quad (16)$$

generates the transition probability from location j to location i of the $k^{th}$ path $$p_{ijk} = \frac{Q_{ji}}{\lambda_k} \frac{\phi_i^{(k)}}{\phi_j^{(k)}} \quad (17)$$

For each transition matrix Eqn. 17, there is a unique stationary distribution associated with each path k:

$$\mu^{(k)} = [\phi^{(k)}]^2, \quad (18)$$

which satisfies $$\mu_i^{(k)} = \sum_j \mu_j^{(k)} p_{ijk}, \quad (19)$$

where $\mu^{(1)}$, associated with the largest eigenvalue $\lambda_1$, corresponds to the maximum entropy stationary distribution. Note that Eqn. 19 is written to emphasize that the squaring operation is performed on a pixel-wise bases. Considering only $\mu^{(1)}$, note that if the Lagrange multipliers take the form $$\gamma_{ij} = \begin{cases} 0 & \text{connected} \\ \infty & \text{not connected} \end{cases} \Rightarrow Q_{ij} = e^{-\gamma_{ij}} = \begin{cases} 1 \\ 0 \end{cases} \quad (20)$$

then Q becomes simply an adjacency matrix A. The maximum entropy distribution constructed from this adjacency matrix is the maximum entropy random walk (MERW). Thus, it is the coupling matrix Q, rather than the adjacency matrix A, that is the fundamental quantity that encodes the coupling information. Another major significant result of the ESP theory to the present problem is that it ranks multiple paths, and these paths can be constructed from arbitrary coupling schemes through $Q_{ij}$. The ESP prior can be incorporated into the estimation scheme by using the coupling matrix $Q_{ij}$ (Eqn. 15) so that $$p(s \mid d, I) = \frac{1}{|2\pi Q|^{1/2}} \exp\left(-\frac{1}{2} s_i^\dagger Q_{ij} s_j\right). \quad (21)$$

Again, it is instructive to consider the simple case of Gaussian noise with this ESP prior where the propagator D in the information Hamiltonian Eq. 5 has the simple form $$D = [Q + \hat{R}^\dagger \Sigma_e^{-1} \hat{R}]^{-1}, \quad (22)$$

where $\Sigma_e$ is defined just after Eqn. 1. Without interactions $H_i = 0$ and using linearly dependent on the data response-over-noise weighted information source $$j = \hat{R}^\dagger \Sigma_e^{-1} d, \quad (23)$$

the propagator Eqn. 22 is similar in form to Eqn. 11, but now has recast the noise corrected propagator in the ESP basis in terms of an interaction free IFT model. The estimate of the signal is the (from either Eqn. 6 and the resulting equivalent of Eqn. 9, or from Eqn. 8 with no interactions)

$$\psi = Dj = Q^+ d \quad (24)$$

where $Q^+ = (Q + \hat{R}^\dagger \Sigma_e^{-1} \hat{R})^{-1} \hat{R}^\dagger \Sigma_e^{-1}$. (25)

Thus, in a similar fashion as discussed in the standard least squares Eqn. 13, the signal is expressed in terms of the eigenmodes of an operator, but this time $Q^+$ rather than the pseudo-inverse of any model functions. ($Q^+$ is not actually a pseudo-inverse—we use the slight abuse of notation with a superscript "+" to draw a similarity with Eqn. 14). Hence, the ESP eigenmodes can be viewed also as free modes of IFT when the noise corrected coupling matrix Q (Eqn. 22) is used as a propagator. However, in general, and in the specific applications examined below, these assumptions are violated and this simple description does not hold. The general EFD formalism, and the algorithm described below, does not depend on this description and no assumption of Gaussian noise is made.

It is important to emphasize a critical feature of the EFD construction at this point. The coupling matrix Q is not constructed from assumed model functions (as in the simple standard least squares example above) but is derived directly from the correlations in the data themselves. Moreover, it is not simply an adjacency matrix but can be constructed (by the user) from any desired coupling scheme consistent with the data and the application. In the EFD method, for example, we may use nearest neighbor interactions, but more complicated interactions are possible as well. Thus, by construction, it may depend on the data in rather complex way, and hence the EFD model expressed by Eqns. 5, 22 and 23, although remaining interaction free, does not possess the property that is a major limitation of many data analysis models in areas ranging from brain imaging to weather related data processing to cosmic microwave background data assimilation—Gaussianity is not assumed in the EFD approach by its very construction.

An important practical implication of the EFD approach is that ESP ranking of eigenmodes allows reduction of the problem dimensions by writing a Fourier expansion using $\{\varphi^{(k)}\}$ as the basis functions $$\psi(\xi_l) = \sum_k^K [a_k \phi^{(k)}(\xi_l) + a_k^\dagger \phi^{\dagger,(k)}(\xi_l)] \quad (26)$$

and keeping number of modes K significantly smaller than the overall size of the problem nN by examining importance of the eigenvalues $\lambda_k$ comparing them to the noise covariance $|\Sigma_e|$. Note that, as a consequence of Eqn. 16, these basis functions are unique once the coupling matrix has been defined. Furthermore, the localization phenomena peculiar to the ESP eigenvectors distinguishes the eigenfunctions used in Eqn. 26 from other harmonic bases.

The information Hamiltonian Eqn. 5 can then be written in ESP basis Eqn. 26 as $$H(d, a_k) = \quad (27)$$

$$-j_k^\dagger a_k + \frac{1}{2} a_k^\dagger \Lambda a_k + \sum_{n=1}^\infty \frac{1}{n!} \sum_{k_1}^K \cdots \sum_{k_n}^K \tilde{\Lambda}_{k_1 \ldots k_n}^{(n)} a_{k_1} \cdots a_{k_n}$$

where matrix $\Lambda$ is the diagonal matrix $\mathrm{Diag}\{\lambda_1, \ldots, \lambda_K\}$, composed of the eigenvalues of the noise corrected coupling matrix, and $j_k$ is the amplitude of kth mode in the expansion of the source j $$j_k = \int j \phi^{(k)}(\xi) d\xi. \tag{28}$$

The expression for the classical solution Eqn. 8 for the mode amplitudes $a_k$ then becomes $$\Lambda a_k = \left( j_k - \sum_{n=1}^{\infty} \frac{1}{n!} \sum_{k_1}^{K} \ldots \sum_{k_n}^{K} \tilde{\Lambda}_{kk_1 \ldots k_n}^{(n+1)} a_{k_1} \ldots a_{k_n} \right). \tag{29}$$

The new interaction terms $\tilde{\Lambda}^{(n)}$ are expressed through integrals over ESP eigenmodes $$\tilde{\Lambda}_{k_1 \ldots k_n}^{(n)} = \int \ldots \int \Lambda_{\xi_1 \ldots \xi_n}^{(n)} \phi^{k_1}(\xi_1) \ldots \phi^{k_n}(\xi_n) d\xi_1 \ldots d\xi_n. \tag{30}$$

The interaction terms $\Lambda^{(n)}$ should be specified in order to be able to estimate amplitudes $\alpha_k$ of the self-interacting modes. The simplest way to take into account the interactions would be an assumption of local only interactions. This can be easily achieved by factorization $\Lambda^{(n)}$ in a product of delta functions $\alpha^{(n)} \delta(\xi_1 - \xi_2) \ldots \delta(\xi_1 - \xi_n)$ where $\alpha^{(n)} < 1$ are constants. This results in a simple, but not particularly useful expression for $\tilde{\Lambda}_{k_1 \ldots k_n}^{(n)}$ $$\tilde{\Lambda}_{k_1 \ldots k_n}^{(n)} = \alpha^{(n)} \int \phi^{k_1}(\xi) \ldots \phi^{k_n}(\xi) d\xi, \tag{31}$$

which after substituting it into Eqn. 29 provides the expression for the classical local-only interacting field recast in the reduced dimensions ESP eigenmodes basis. To obtain a more interesting (and more practically useful) expression for estimating amplitudes of interacting modes, we may assume that the nonlinear interactions between different modes will reflect the coupling. A natural way to take coupling into account would be through factorization of $\Lambda^{(n)}$ in powers of the coupling matrix, i.e., we can assume that $$\Lambda_{\xi_1 \ldots \xi_n}^{(n)} = \frac{\alpha^{(n)}}{n} \sum_{p=1}^{n} \prod_{\substack{m=1 \\ m \neq p}}^{n} Q_{\xi_p \xi_m}, \tag{32}$$

which results in $$\tilde{\Lambda}_{k_1 \ldots k_n}^{(n)} = \frac{\alpha^{(n)}}{n} \sum_{p=1}^{n} \left( \frac{1}{\lambda_{k_p}} \prod_{m=1}^{n} \lambda_{k_m} \right) \int \left( \prod_{r=1}^{n} \phi^{k_r}(\xi) \right) d\xi. \tag{33}$$

Here, values of the coefficients $\alpha^{(n)}$ should be chosen sufficiently small to ensure the convergence of the classical solution Eqn. 29. From a practical standpoint values of $\alpha^{(n)} \leq 1/\max(j_k^n/\lambda_k)$ provide good starting estimate for further adjustments.

This expression is correct up to the third (n=3) order but discards various chain-like factorizations (e.g., $Q_{\xi_1 \xi_2}$, $Q_{\xi_2 \xi_3} \ldots Q_{\xi_{n-1} \xi_n}$) for higher (n>3) orders. These chain-like terms may be included as well by re-expanding required nonlinear combinations of ESP basis functions through the same basis. We would like to emphasize that this task is not impracticable as in many "real life" applications, the ESP eigenmodes are expected to be compactly localized because of the unique localization properties of the ESP eigenvectors. Therefore, nonlinear expressions that involve various powers of ESP eigenmodes can be expected to decay significantly faster than nonlinear terms expressed either through the whole domain integration or with the traditional trigonometric functions or polynomials used in the whole domain Fourier-like expansions. Nevertheless, this fact was neither explored nor used to obtain the results presented in the following sections.

It should be recognized that the traditional trigonometric functions and polynomials (e.g., Legendre or Chebyshev) have an important advantage when used as basis functions, especially for deriving analytical relations—their nonlinear forms can easily be expressed through the linear forms by using simple recurrence formulas, i.e., as simple as frequency scaling for the exponentials. Besides, in many practical applications temporal variations are well-characterized by frequency modes and thus, instead of using the ESP expansion in the whole space-time domain Eqn. 26, it may often be beneficial to use ESP basis only for spatial coordinates $\{x_i\}$ while keeping the traditional Fourier polynomial expansion in the temporal $\{t_j\}$ domain $$\psi(x_i, t_j) = \sum_{k,l} [a_{k,l} e^{i\omega_l t_j} \phi^{(k,l)} + a_{k,l}^\dagger e^{-i\omega_l t_k} \phi^{\dagger,(k,l)}] \tag{34}$$

Note, that the coupling matrix Q is now different at different frequencies $\omega_l$, hence, spatial ESP basis functions $\phi^{(k,l)}$ depend on frequency as well. Except for the appearance of the second index in this form of expansion, the rest of the approach, including the information Hamiltonian Eqn. 27 and the form of the interaction terms Eqn. 32 can easily be recast using this new basis.

We would like to stress once more that this non-Gaussian and non-linear EFD approach represents a natural special case of the very general Information Field Theory (IFT) for this particular type of prior information and can produce solutions using all the useful techniques, including Feynman diagrams, or just by using any suitable iterative method for the classical solution of Eqn. 29. In the following discussion, we illustrate the EFD method using several simple models of spatially non-overlapping and overlapping time periodic and non-periodic sources, and show that using simple anharmonic terms Eqn. 32 in the interaction Hamiltonian Eqn. 27 allows reliable and natural identification and separation of spatially overlapping non time periodic modes, a task which is important in many (unrelated) areas that require analysis of spatio-temporal data.

Implementation

The general EFD formalism is very flexible and allows for multiple spatial and temporal correlation orders to be incorporated, and can include a wide range of prior information, such as physiological models for the FMRI signal. However, for brevity, we limit our implementation to nearest neighbor interactions (in both space and time) and a Gaussian noise model. Nevertheless, this rather straightforward implementation is sufficient to demonstrate the power and utility of the method. Two slightly different implementations were used, the first was using a complete spatial-temporal ESP basis for signal expansion (Eqn. 26), and the second was based on spatial ESP but employed Fourier expansion in the temporal domain (Eqn. 34). All the algorithms described herein were written in standard ANSI C/C++. The spatio-temporal EFD procedure used for estimating the signal modes consisted of the following steps:

(i) Generate coupling matrix Eqn. 15 using simple nearest neighbor coupling $Q(\xi_i, \xi_j)=d(\xi_i)d(\xi_j)A_{ij}$, where is the space-time adjacency matrix, i.e., $A_{ij}$ equals 1 if i and j are nearest neighbors in space or time domains, and 0 otherwise.
(ii) Find ESP eigenvalues $\lambda_k$ and eigenvectors $\varphi^{(k)}$ for the coupling matrix $Q(\xi_i, \xi_j)$ solving the eigenvalue problem Eqn. 16.
(iii) Use ESP eigenvalues $\lambda_k$ and eigenvectors $\varphi^{(k)}$ to construct the information Hamiltonian Eqn. 27, where $\Lambda$ is the diagonal matrix $\mathrm{Diag}\{\lambda_1, \ldots, \lambda_K\}$ of ESP eigenvalues, and the interaction terms $\Lambda^{(n)}$ are constructed from ESP eigenvalues and eigenvectors with the help of Eqn. 33.
(iv) Finally, the amplitudes $a_k$ that describe both spatially and temporally interacting modes of the information Hamiltonian Eqn. 27 are found from the nonlinear expression for the classical solution Eqn. 29.

The alternative implementation (corresponding to Eqn. 34) although follows the above estimation steps nevertheless has several important differences that are worth mentioning. First, instead of generating nearest neighbor coupling both in space and time domains, it employs frequency dependent spatial coupling matrix $Q(x_i, x_j, \omega_l)$, taking nearest neighbor coupling only in spatial domain (here, $x_i$ and $x_j$ are spatial coordinates, and $\omega_l$ is a frequency). Second, the strength of coupling for each frequency depends on the temporal pair correlation function. There are different ways to introduce this temporal correlation dependence. We used the following form of coupling matrix $$Q(x_i, x_j, \omega_0) = \mathcal{R}_{ij}^m d(x_i, \omega_0) d(x_j, \omega_0), \quad (35)$$

$$Q(x_i, x_j, \omega_l) = \mathcal{R}_{ij}^m (\varphi^{(1)}(x_i, \omega_0) d(x_j, \omega_l) + \varphi^{(1)}(x_j, \omega_0) d(x_i, \omega_l)), \quad (36)$$

where $\mathcal{R}_{ij}$ is either the mean $$\mathcal{R}_{ij} = \frac{1}{T}\int_0^T \int (d(x_i, t-\tau)d(x_j, \tau))d\tau dt \quad (37)$$

or the maximum $$\mathcal{R}_{ij} = \max_t \int d(x_i, t-\tau)d(x_j, \tau)d\tau \quad (38)$$

of the temporal pair correlation function computed for spatial nearest neighbors i and j, $\varphi^{(1)}(x_j, \omega_0)$ is the eigenmodes that corresponds to the largest eigenvalue of $Q(x_i, x_j, \omega_0)$, and the exponent $m \geq 0$ is used to attenuate the importance of correlations.

The additional implementation steps can be summarized then as follows:
(i) Generate the temporal pair correlation functions $R_{ij}$ for every i and j pair of spatial nearest neighbors. For example, for FMRI data, the correlation functions will be generated for every voxel in the vicinity of each voxel.
(ii) Compute the mean (or largest) correlation value for each pair and use this as a coupling coefficient from the propagator to find the spatial eigenmodes $\varphi(x_i, \omega_0)$ with zero frequency $\omega_0$ (that is, the mean field by solving the eigenvalue problem Eqn. 16 for the coupling matrix $Q(x_i, x_j, \omega_0)$ from Eqn. 35.
(iii) Use the zero frequency spatial eigenmodes $\varphi(x_i, \omega_0)$ to construct coupling matrices $Q(x_i, x_j, \omega_l)$ in Eqn. 36 and solve the eigenvalue problem Eqn. 16 for each $\omega_l$ frequency.
(iv) Generate the information Hamiltonian Eqn. 27 by summation of input from interaction terms Eqn. 33 and solve for the mode amplitudes $a_k$ in a way similar to the last two items of the spatio-temporal approach.

The first three steps determine the values of mean field at every spatial position and then determine the spatio-temporal eigenmodes in spatial-frequency (i.e., Fourier) space assuming non-interacting fields. The last step determines the interactions between these eigenmodes. The final results are space/time localization patterns that are our definition of the "modes" of the data. An important advantage of the EFD method is that it does not require any reference feature (voxel or other point) as would be needed in a standard correlation analysis.

EXAMPLES

To illustrate the capabilities of the EFD method, the method was applied to two toy (simulated) test cases and then to two real data sets. The first toy example is inspired by FMRI and is easily amenable to idealized simulations, serving as a good paradigms to test and validate the EFD method and compare it to existing methods. The second example is also a reasonable model for the situation faced in the analysis of mobile Doppler radar data. The third and fourth examples provide a demonstration of the EFD method on two real data sets that are part of ongoing research in our lab: resting state FMRI data and mobile Doppler radar data from a tornadic supercell thunderstorm, respectively.

Example 1: Simulated 2D Data

In "traditional" FMRI, a subject is presented with a well-defined input stimulus, such as a visual stimulation consisting of a rapidly flashing (e.g., 8 Hz) checkerboard that is presented for a short period (e.g., 10 sec), turned off for the same period, and this pattern of presentation is repeated several times, resulting in a so-called "block stimulus design." This is an example of task-based FMRI, so-called because the input task (the stimulus) is known. While the relationship between the input stimulus and the FMRI signal is actually quite complicated, it is often quite close to the stimulus. Thus, simple correlation of the input stimulus (perhaps convolved with a neuronal response function) with the signal is a useful and established analysis method, as long as the signals are not spatially or temporally overlapping. If they are, traditional correlation analysis methods fail and most sophisticated techniques such as ICA have been employed, though are known to be insufficient, even in relatively simple cases. The first example is one such simple case in which the state-of-the-art ICA method fails whereas EFD is able to recover the correct signals and thus provides a rather simple but powerful demonstration of EFD capabilities that can be directly compared with ICA results.

A direct comparison with ICA in a simple, idealized numerical model of brain activation will serve to illustrate the essential features of the EFD method. Consider two partially overlapping ellipsoidal spatially "activated" regions with two different low signal-to-noise (SNR) square wave signals in Gaussian noise.

Figure 3A:
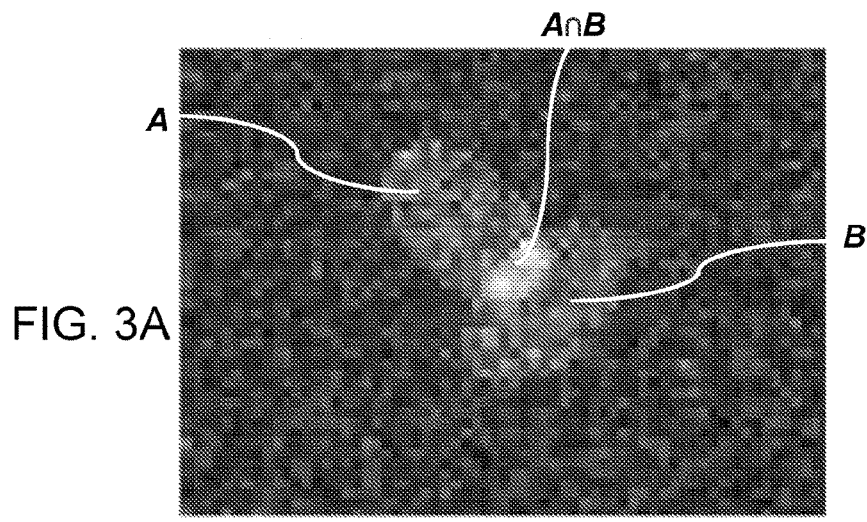
FIGS. 3A-3L provide a comparison of analysis of a simulated task-based fMRI signals plotted spatially (FIG. 3A) and temporally (FIGS. 3B-3D) using EFD (FIGS. 3F-3H) and using prior art ICA (FIGS. 3I-3L).
Figure 3B:
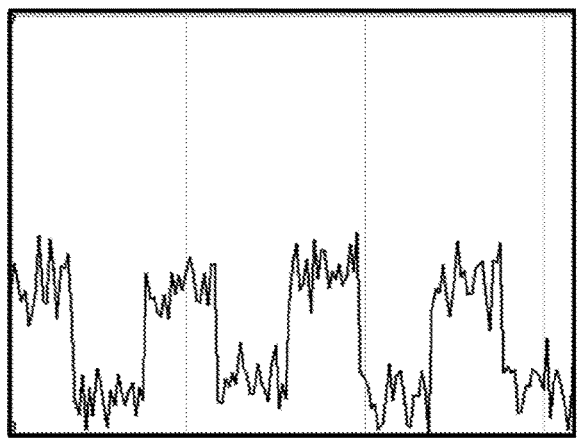
Figure 3C:
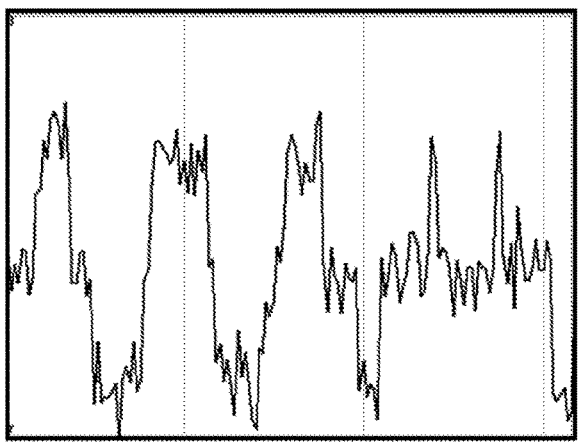
Figure 3D:
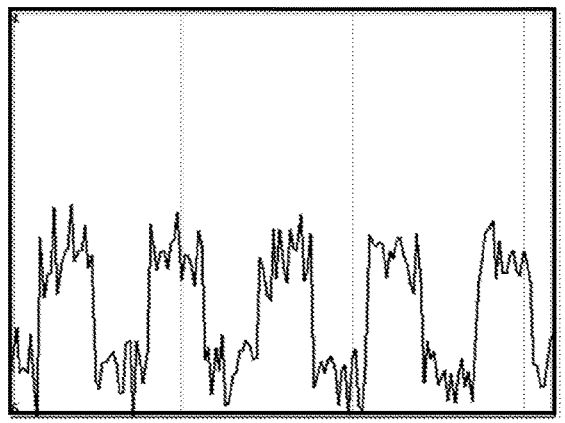
Figure 3E:
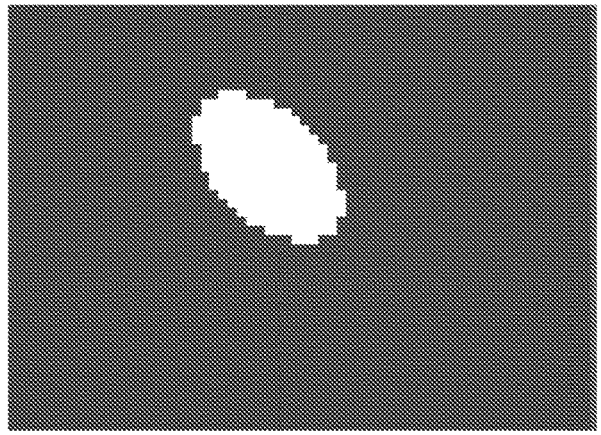
Figure 3F:
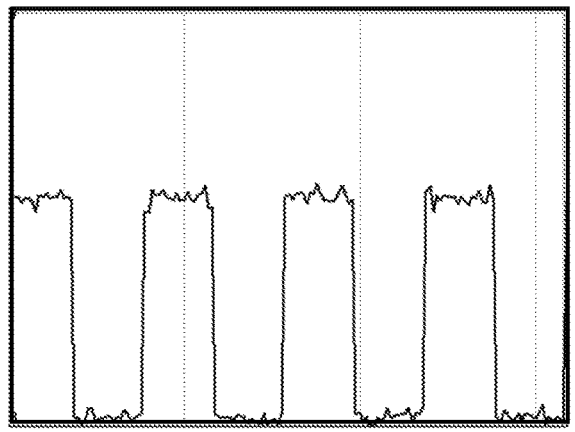
Figure 3G:
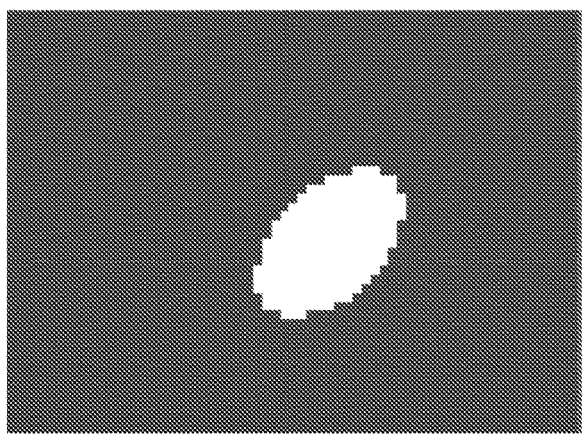
Figure 3H:
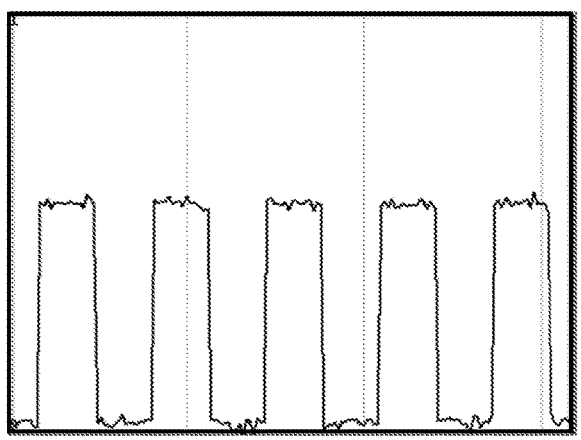
Figure 3I:
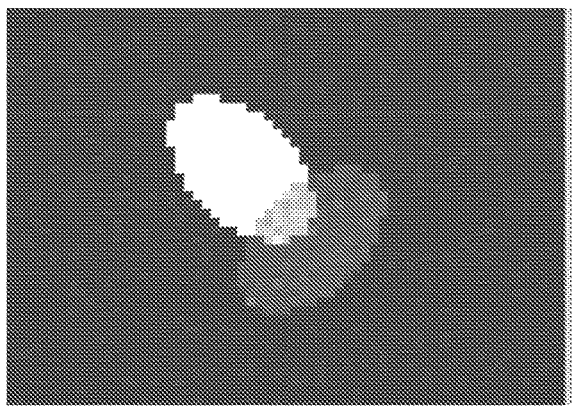
Figure 3J:
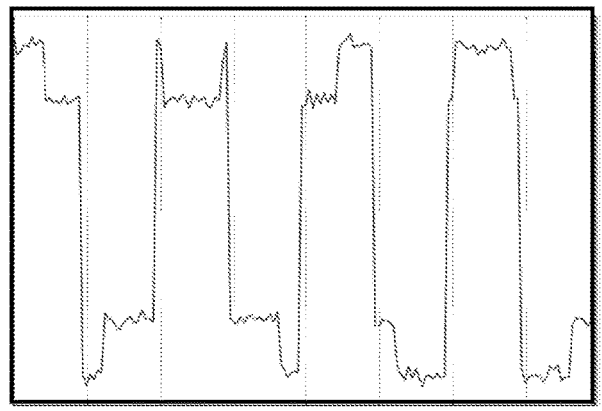
Figure 3K:
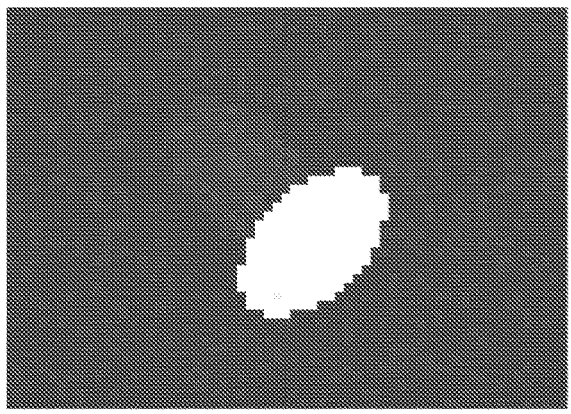
Figure 3L:
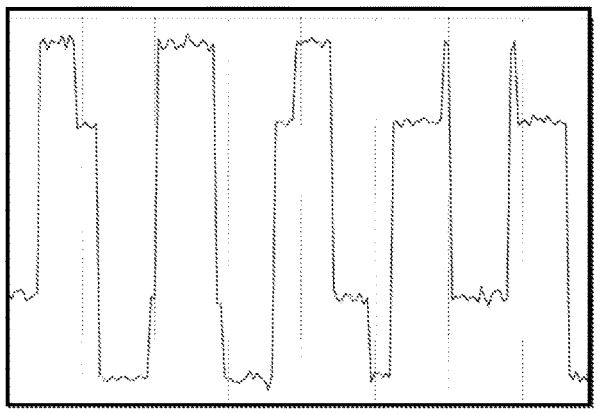

The square wave pattern is an idealization of the simplest FMRI experiment (often called "task based" FMRI) in which a subject is presented with a stimulus that is turned on and off at regular intervals and the brain regions activate in concert with the stimulus. This particular example would thus represent a brain presented with two diff t stimuli which selectively activate the two ellipsoidal regions. The signals from the two regions are assumed to be additive. The brain activation patterns from a true rsFMRI experiment are much more complicated than this example, being non-linear, coupled and in three spatial dimensions, so this test should represent a simple benchmark for the efficacy of any proposed rsFMRI method. FIGS. 3A-3L provide a comparison of EFD with ICA in task-based fMRI simulation. FIG. 3A illustrates the simulated signals with additive Gaussian noise so that the signal-to-noise is SNR=2.5. The spatial dimensions are (64×64 voxels) and there are 160 time points. FIGS. 3B, 3C and 3D are plots of the time course in region A, in region A and B overlapping, and in region B, respectively. FIGS. 3E-3F show the estimated modes using EFD, where FIG. 3E shows the estimated power in mode 1 and FIG. 3F plots the estimated power in mode 1. FIGS. 3G and 3H show and plot the estimated power in mode 2. The cutoff for defining "relevant" modes was determined by the ratio of the mode powers and was set to −30 dB signal attenuation. FIGS. 3I-3L show the estimated modes (modes 1 and 2, in the same combination shown for the EFD results) using ICA. All voxels in region A have the same time course (4 cycles) and all voxels in region B have the same time course (5 cycles). The EFD analyses are shown in the middle row. Only two modes are detected and these are seen to correspond to the correct spatial regions with the correct temporal profiles. EFD has thus identified the correct space-time regions of the signals.

On the other hand, the ICA results shown in FIGS. 3I-3L are erroneous. The components are a mixture in both space and time of the two true modes. While the algorithm undoubtedly constructs two "independent" components, this example clearly illustrates that this is a poor model for even this simple brain activation model, and thus most likely for actual brain activation data. Indeed, the signal modes are not independent in that they share at least some portion of the same space-time region. Requiring them to be maximally independent is thus forcing on them a property they do not intrinsically have. The EFD procedure, on the other hand, simply constructs the most probable pathways in space-time based on the measured correlations in the data. Because of the localization properties of ESP (first observed in the maximum entropy random walk), there are, in fact, very few space-time parameter configurations consistent with the prior coupling information. The "modes" thus represent the configurations that are consistent with the data and the most probable. We would like to reiterate that the simplicity of this example was for demonstrative purposes but emphasize that the EFD methods does not assume Gaussian noise, simple additivity of the signal, or linearity of the signal.

Example 2: Simulated 3D Non-Periodic, Overlapping Data

The second toy example is an idealization of the more practical situation faced in many scientific applications, including our own particular cases of FMRI and mobile Doppler radar data and consists of mixing different time varying signals inside several three-dimensional spatial domains. This is a model for the second "flavor" of FMRI is the acquisition data while the subject is not presented with any stimulus and is simply "resting". This is called "resting state FMRI", or rsFMRI, and the analysis of the detected spatio-temporal fluctuations presents a tremendous challenge because they are characterized by being non-linear, non-periodic, and spatially and temporally overlapping, and there is no known input stimulus with which to compare these fluctuations as they are thought to be due to "intrinsic" modes of brain activity. This example is also a reasonable idealized model for the problem faced in mobile Doppler radar data from severe thunderstorms, where complex spatio-temporal variations in the detected reflectivity and wind speeds are driven by complex storm dynamics characterized by coherent variations in dynamical parameters such as vertical vorticity and vorticity stretching.

Figure 4:
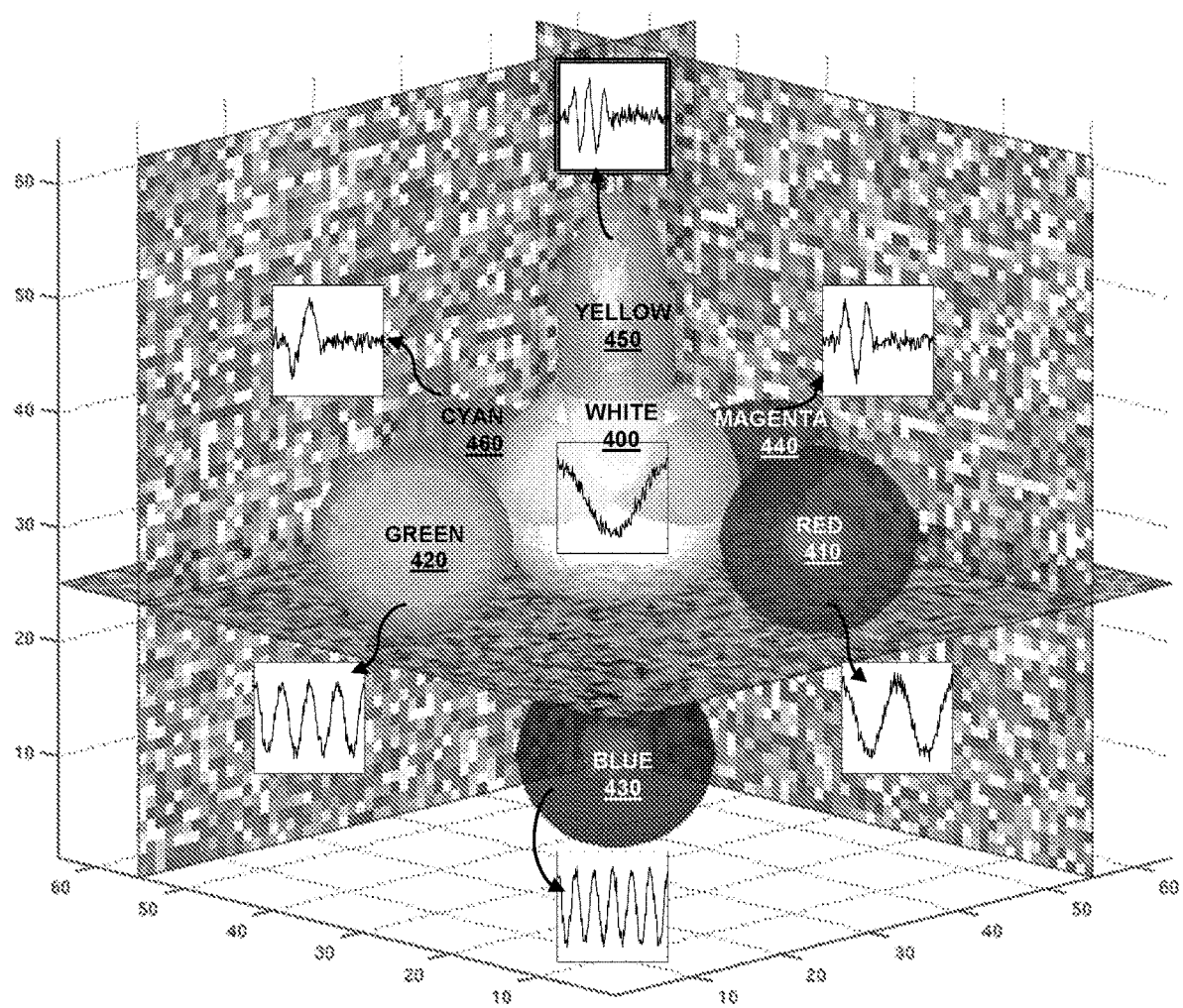
FIG. 4 is a toy example of spatio-temporal data with non-periodic and spatially overlapped regions.

The simulation with seven non-periodic and spatially overlapped regions embedded within a three-dimensional Cartesian lattice, with amplitudes that vary in time. As shown in FIG. 4, the simulation includes a central sphere ("white" (400)) located at the origin ($\{x, y, z\}=\{0, 0, 0\}$) oscillating at a single, periodic frequency (indicated by the inset superimposed over the sphere in the figure), surrounded by six spherical or ellipsoidal regions along the principal axes $\{x_1, 0, 0\}$, $\{-x_2, 0, 0\}$, $\{0, y_1, 0\}$, $\{0, -y_2, 0\}$, $\{0, 0, z_1\}$, $\{0, 0, -z_2\}$. The signals are the same throughout the volume of any particular domain. In addition, Gaussian noise has been added. Three spheres (red (410), green (420), blue (430)), spatially separated from the central sphere, each oscillate at a single, distinct frequency, though at different maximum amplitudes, as indicated by the inset plots associated with each sphere. Three ellipsoids (magenta (440), yellow (450) and cyan (460)) overlap the central sphere 400 and have non-periodic time courses (again with different maximum amplitudes) created by filtering a sinusoidal amplitude with a Fermi filter, which turns the signal on and off smoothly in time. The signal associated with each ellipsoid is illustrated via the inset pointed to by its respective ellipsoid by a black arrow. The width of the Fermi filter is 30% of the length of the time series with a transition width of 2 time points. The filter begins 30% of the way into the time series. Both the periodic and non-periodic objects overlap spatially, such that in the center area of the white sphere, signals from four different objects are mixed (one periodic signal from the white sphere itself and three different non-periodic signals from the magenta (440), yellow (450) and cyan (460) ellipsoids). This example illustrates the important fact that extracted EFD modes need not be orthogonal. This is crucial in many, if not most, applications, such as in the case of rs-FMRI data below, where one would not expect the data modes to be orthogonal.

Figure 5A:
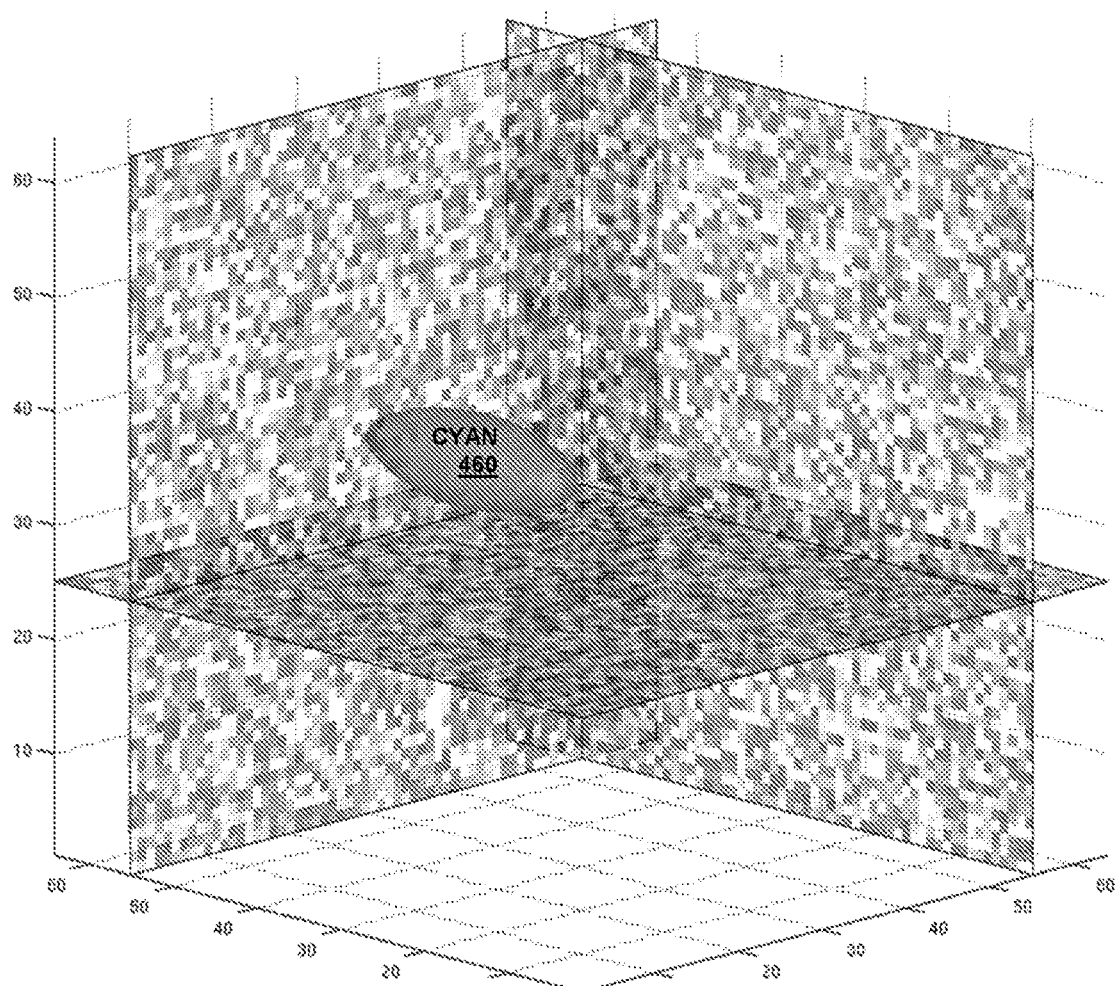
FIGS. 5A-5F illustrate spatial (FIGS. 5A, 5C and 5E) and temporal patterns (FIGS. 5B, 5D and 5F) extracted from three ellipsoids shown in the toy problem of FIG. 4.
Figure 5B:
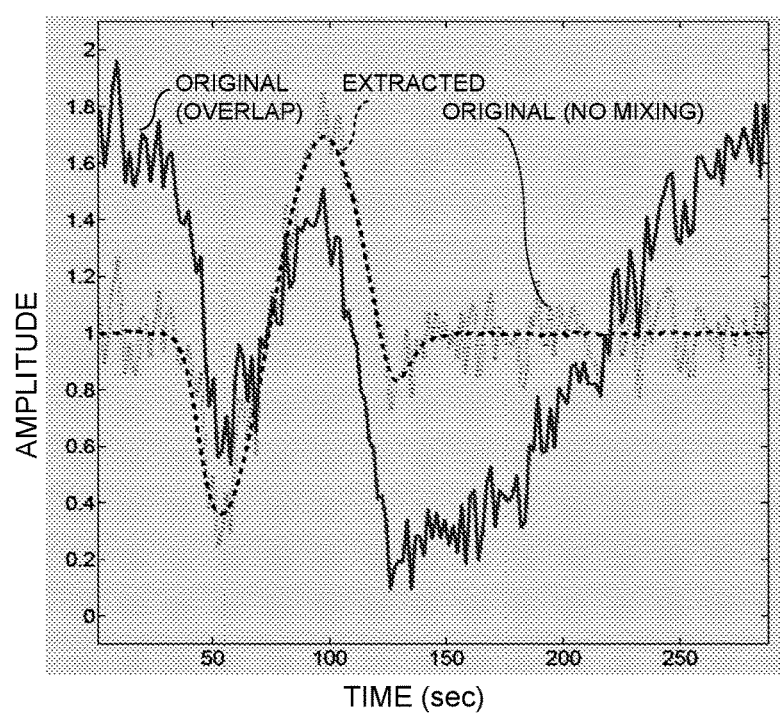
Figure 5C:
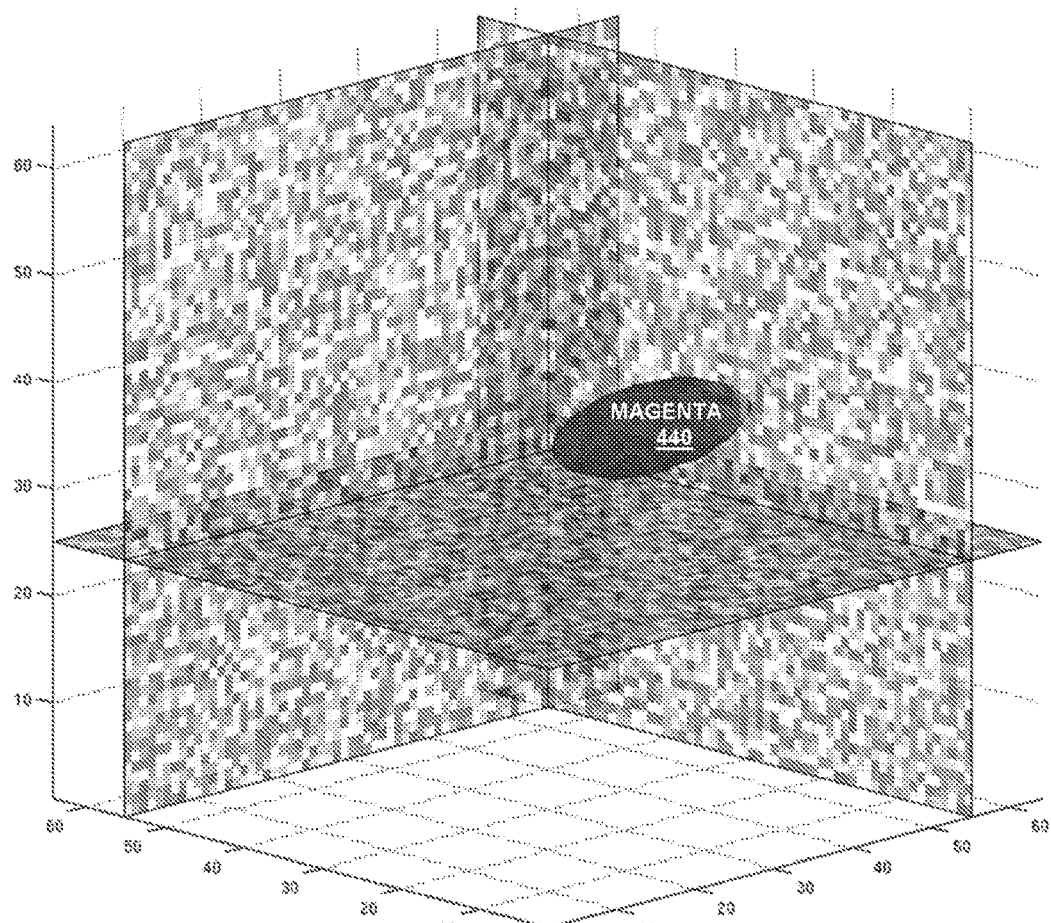
Figure 5D:
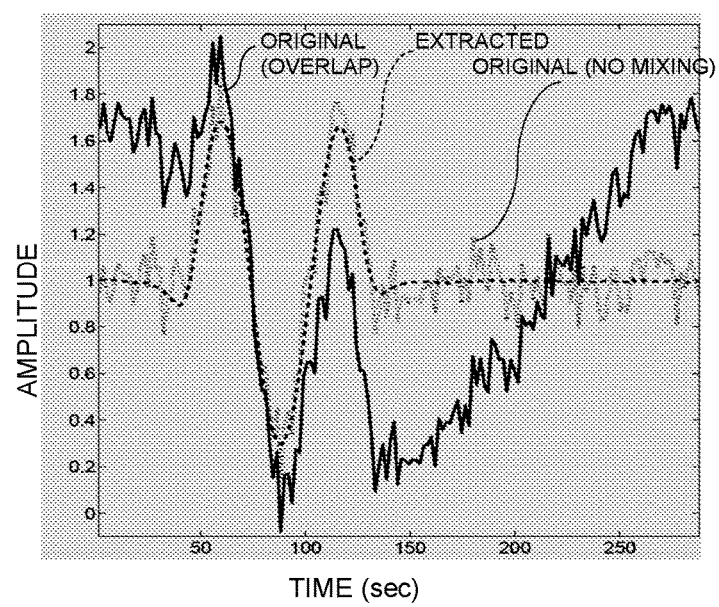
Figure 5E:
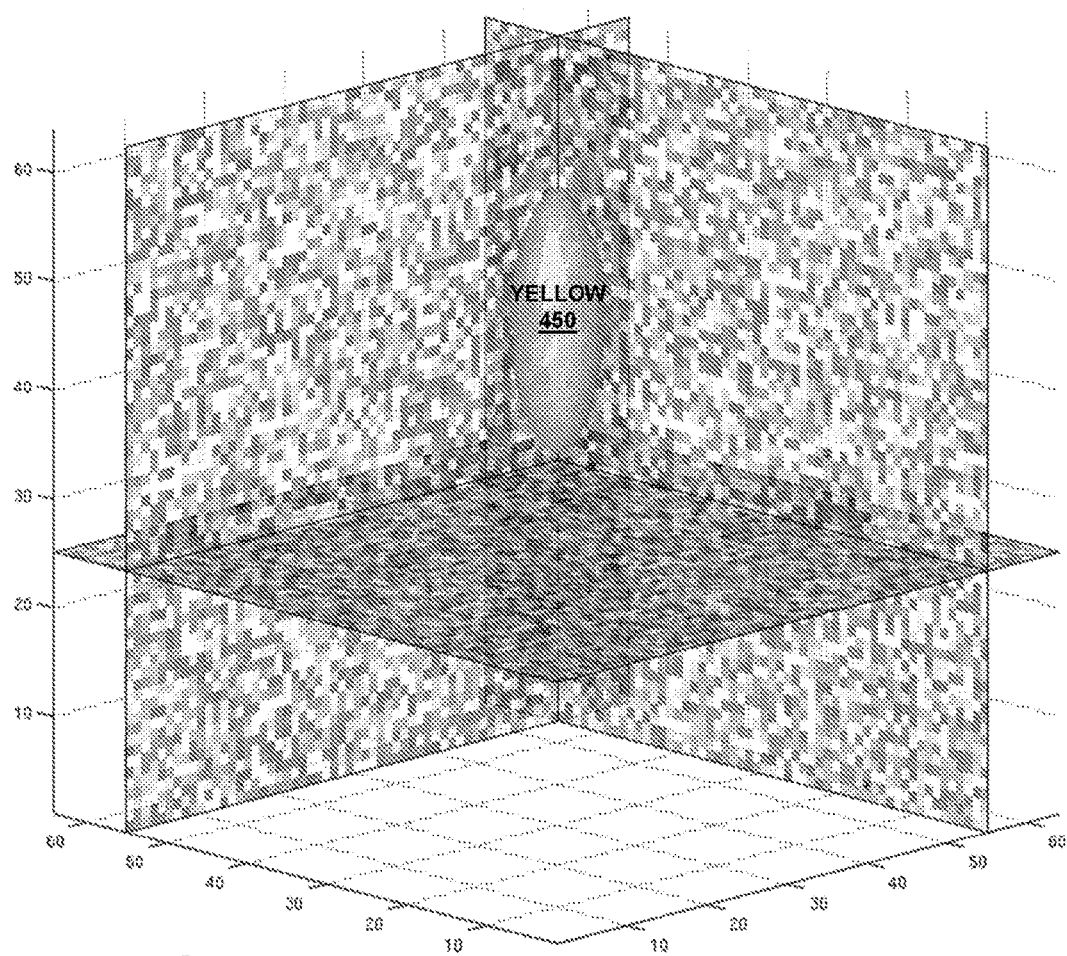
Figure 5F:
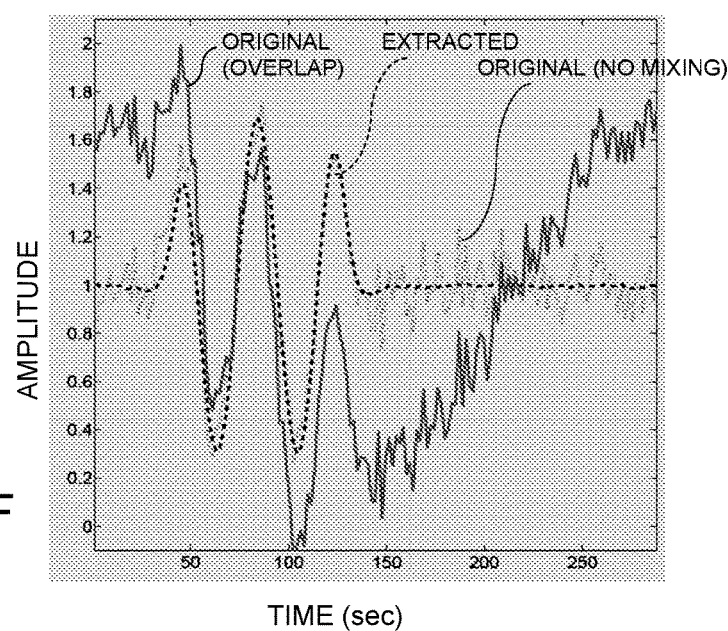

FIGS. 5A-5F illustrate the spatial (FIGS. 5A, 5C, and 5E) and temporal patterns (FIGS. 5B, 5D, and 5F) of extracted modes for temporally non-periodic ellipsoids 440, 450 and 460, respectively, that overlap with each other and with a periodically oscillating central sphere 400. The time sequences shown in FIGS. 5B, 5D, and 5F illustrate the original signals in the overlap region of each ellipsoid (solid line) and the extracted signal (black dashed line). The original signal from the isolated regions (without mixing with the signal from the neighboring overlapping areas) are also included with dotted lines. As the whole volume is submerged in Gaussian noise with $\sigma=0.1$ the signal for all spheres corresponds to a signal-to-noise of SNR 6.8 to 7.

Figure 6A:
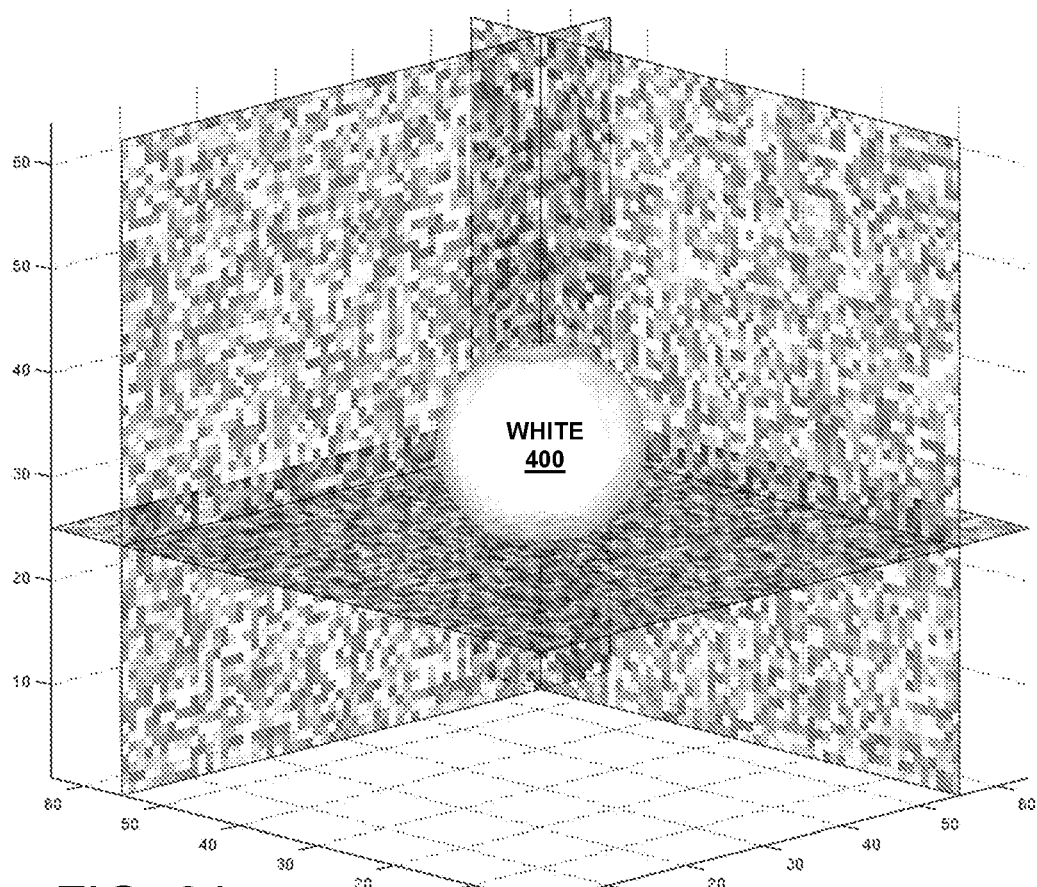
FIGS. 6A-6D illustrate spatial (FIG. 6A) and temporal (FIG. 6B) patterns of extracted modes for the central sphere in FIG. 4.
Figure 6B:
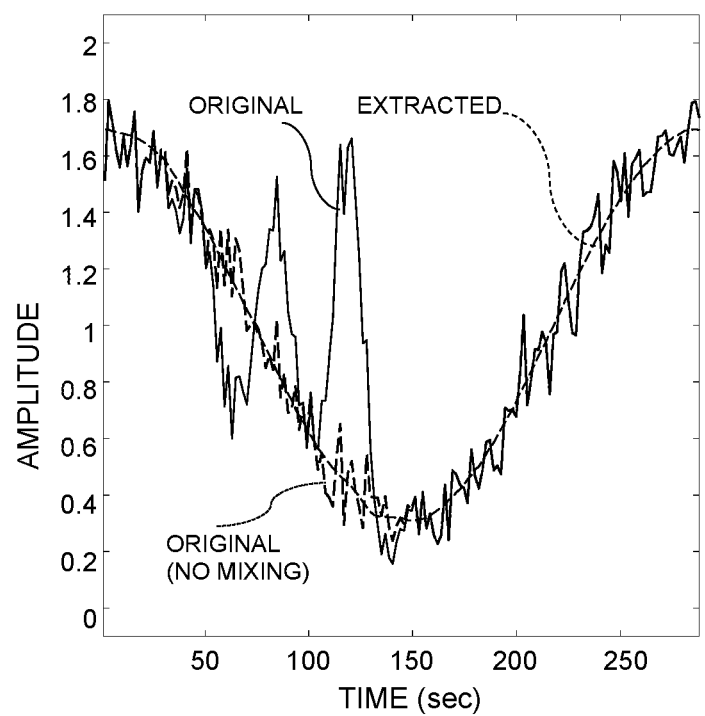
Figure 6C:
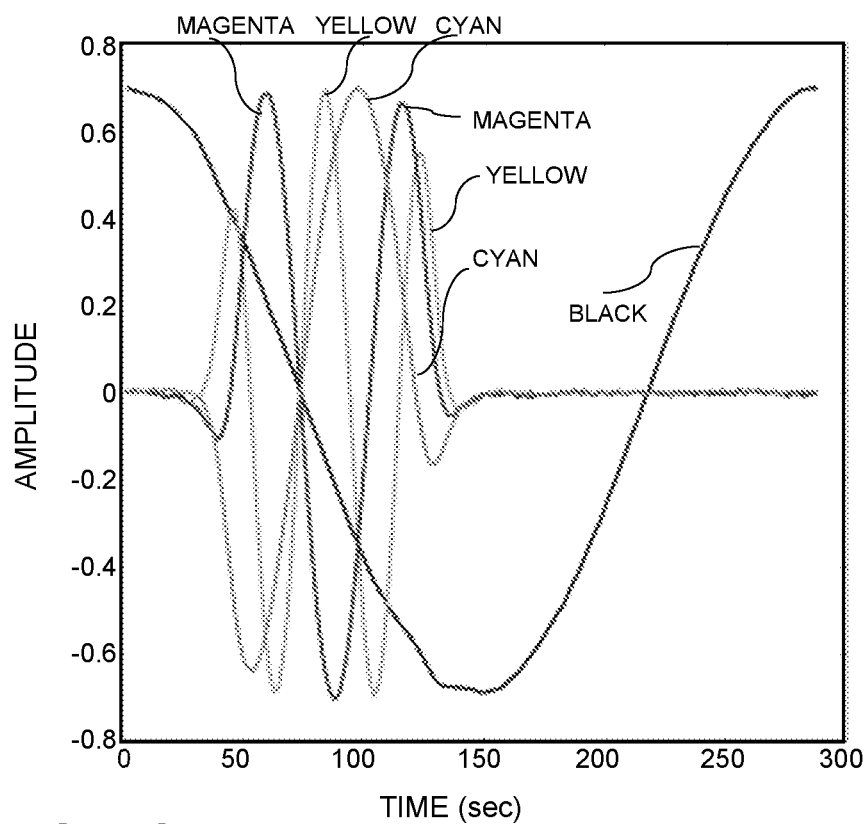
Figure 6D:
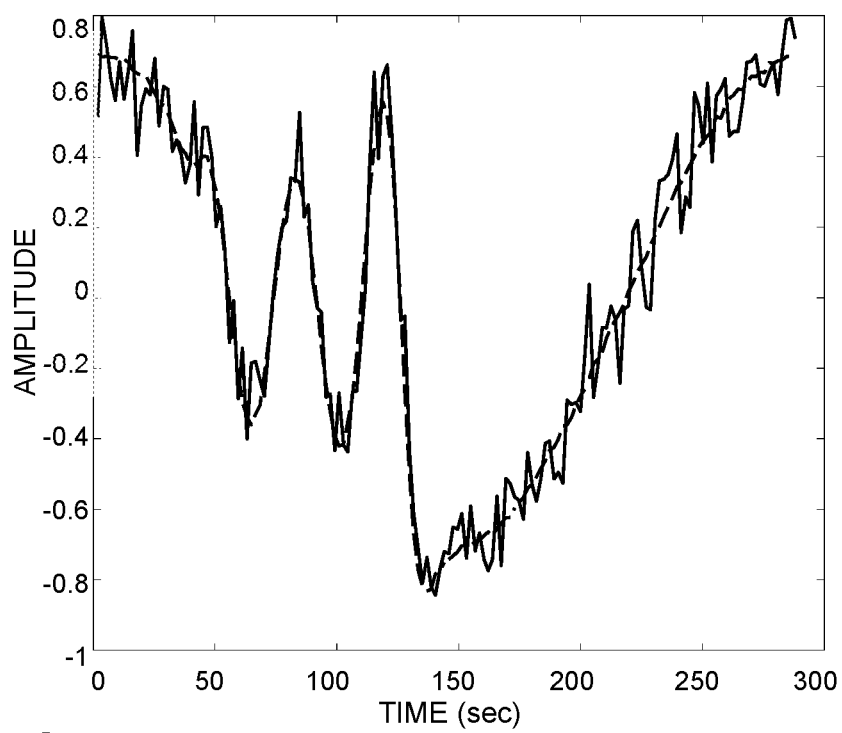

FIGS. 6A and 6B show the spatial and temporal patterns, respectively, of the extracted mode for the central overlapping sphere 400. This sphere overlaps with three neighboring ellipsoids (cyan 460, magenta 440 and yellow 450), all four different signals contribute to the overall signal at the center area of the white sphere. The time sequence in FIG. 6B shows the original signals at the center of the white sphere (solid line) and the extracted signal (dashed line). The original signal from the isolated white sphere (without mixing with the signal from all four neighboring overlapping regions) is also shown by the dotted lines. In FIG. 6C, restored signals for all four modes that give input to the original signal at the central area are plotted (signals from magenta, yellow, cyan ellipsoids, and gray sphere). FIG. 5D shows this original noisy signal (solid line) and the sum of all four restored signals (dashed line).

To further demonstrate the broad utility of the EFD method, we provide results for data analysis of two datasets from completely unrelated areas, both from physical and informational sense. The first example is based on biological data—human resting state functional magnetic resonance imaging (rs-FMRI) data. An atmospheric data from a mobile Doppler radar system was used for the second example.

Example 3: Resting State FMRI Data

FIG. 1 provides a block diagram of an exemplary magnetic resonance (MR) imaging system 200 in accordance with various embodiments. The system 200 includes a main magnet 204 to polarize the sample/subject/patient; shim coils 206 for correcting inhomogeneities in the main magnetic field; gradient coils 206 to localize the MR signal; a radio frequency (RF) system 208 which excites the sample/subject/patient and detects the resulting MR signal; and one or more computers 226 to control the aforementioned system components.

A computer 226 of the imaging system 200 comprises a processor 202 and storage 212. Suitable processors include, for example, general-purpose processors, digital signal processors, and microcontrollers. Processor architectures generally include execution units (e.g., fixed point, floating point, integer, etc.), storage (e.g., registers, memory, etc.), instruction decoding, peripherals (e.g., interrupt controllers, timers, direct memory access controllers, etc.), input/output systems (e.g., serial ports, parallel ports, etc.) and various other components and sub-systems. The storage 212 includes a computer-readable storage medium.

Software programming executable by the processor 202 may be stored in the storage 212. More specifically, the storage 212 contains software instructions that, when executed by the processor 202, causes the processor 202 to acquire multi-shell diffusion weighted magnetic resonance (MRI) data in the region of interest ("ROI") and process it using a spherical wave decomposition (SWD) module (SWD module 214); compute entropy spectrum pathways (ESP) (ESP module 216); perform ray tracing using a geometric optics tractography algorithm (GO module 218) to generate graphical images of fiber tracts for display (e.g., on display device 210, which may be any device suitable for displaying graphic data) the microstructural integrity and/or connectivity of ROI based on the computed MD and FA (microstructural integrity/connectivity module 224). More particularly, the software instructions stored in the storage 212 cause the processor 202 to display the microstructural integrity and/or connectivity of ROI based on the SWD, ESP and GO computations.

Additionally, the software instructions stored in the storage 212 may cause the processor 202 to perform various other operations described herein. In some cases, one or more of the modules may be executed using a second computer of the imaging system. (Even if the second computer is not originally or initially part of the imaging system 200, it is considered in the context of this disclosure as part of the imaging system 200.) In this disclosure, the computers of the imaging system 200 are interconnected and are capable of communicating with one another and performing tasks in an integrated manner. For example, each computer is able to access the other's storage.

In other cases, a computer system (similar to the computer 226), whether being a part of the imaging system 200 or not, is used for post-processing of diffusion MRI data that have been acquired. In this disclosure, such a computer system comprise one or more computers and the computers are interconnected and are capable of communicating with one another and performing tasks in an integrated manner. For example, each computer is able to access another's storage. Such a computer system comprises a processor and a computer-readable storage medium (CRSM). The CRSM contains software that, when executed by the processor, causes the processor to obtain diffusion magnetic resonance (MRI) data in region of interest (ROI) in a patient and process the data by performing spherical wave decomposition (SWD), entropy spectrum pathway (ESP) analysis and applying geometric optics algorithms to execute ray tracing operations to define fiber tracts for display on a display device.

The resting state FMRI data were from a single subject from a previously published study (C. W. Wong, et al., 2013 *Neuroimage* 83 983-990). All data were collected post-administration of 200 mg of caffeine. Blood oxygenation level dependent (BOLD) imaging data were acquired on a 3 Tesla GE Discovery MR750 whole body system using an eight channel receiver coil. High resolution anatomical data were collected using a magnetization prepared 3D fast-spoiled gradient (FSPGR) sequence (TI=600 ms, TE=3.1 ms, flip angle=8 degrees, slide thickness=1 mm, FOV=25.6 cm, matrix size=256×256×176). Whole brain BOLD (blood oxygenation level dependent) resting-state data were acquired over thirty axial slices using an echo planar imaging (EPI) sequence (flip angle=70 degrees, slice thickness=4 mm, slice gap=1 mm, FOV=24 cm, TE=30 ms, TR=1.8 s, matrix size=64×64×30.)

Field maps were acquired using a gradient recalled acquisition in steady state (GRASS) sequence (TE1=6.5 ms, TE2=8.5 ms), with the same in-plane parameters and slide coverage as the BOLD resting-state scans. The phase difference between the two echoes was then used for magnetic field inhomogeneity correction of the BOLD data. Cardiac pulse and respiratory effect data were monitored using a pulse oximeter and a respiratory effort transducer, respectively. The pulse oximeter was placed on each subject's right index finger while the respiratory effort belt was placed around each subject's abdomen. Physiological data were sampled at 40 Hz using a multi-channel data acquisition board.

Figure 7A:
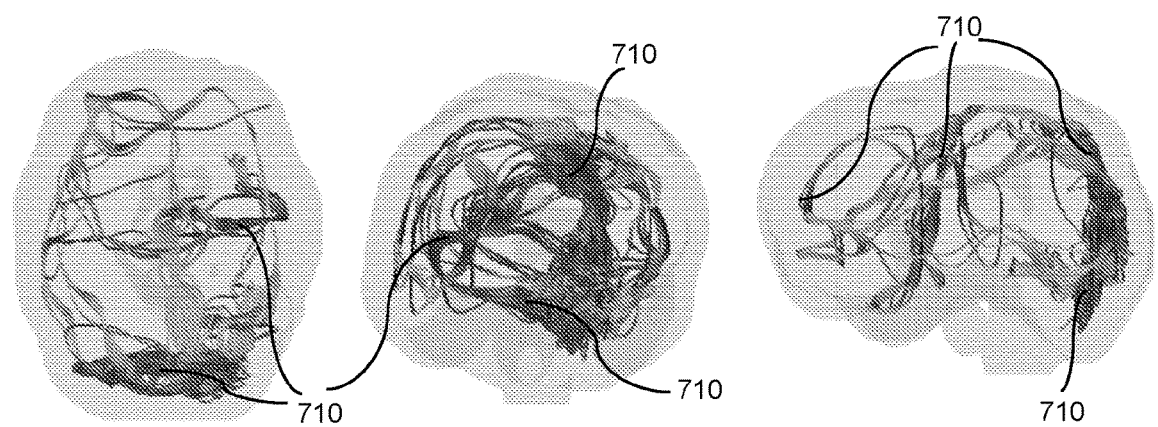
FIGS. 7A and 7B show images of functional tractography and functional eigentracts, respectively, viewed from the top, rear and side of the subject's head.
Figure 7B:
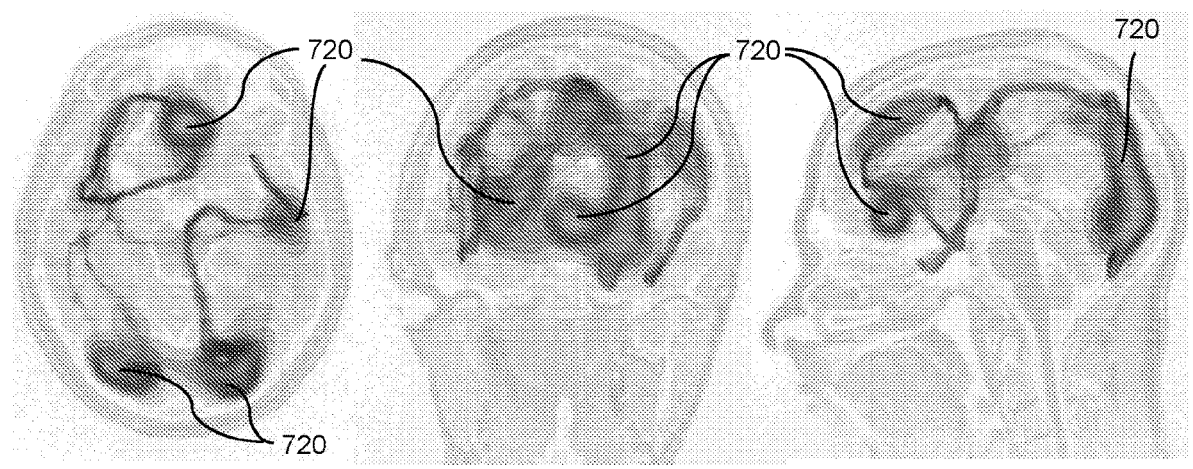

Results of the EFD analysis are shown in FIGS. 7A and 7B, which show the functional tractography and functional eigentracts, respectively, viewed from the top, rear and side of the subject's head. The power in a single (arbitrarily chosen) mode (the 5th) is shown in the shaded contours 720 in FIG. 7B, along with the first eigenmode ((darker) contours 710) of the functional tractography in FIG. 7A. The functional tractography was seeded by the high probability regions of the power. In this dataset, twenty-three significant modes were detected. These modes have significant overlap in both space and time with one another. However, they are distinct modes because they do not have overlapping spatio-temporal regions. Aside from the initial data preparation described by Wong et al., no processing other than the EFD algorithm described above was used. In particular, no noise filtering of any kind was employed.

Example 4: Tornadogenesis

Figure 2:
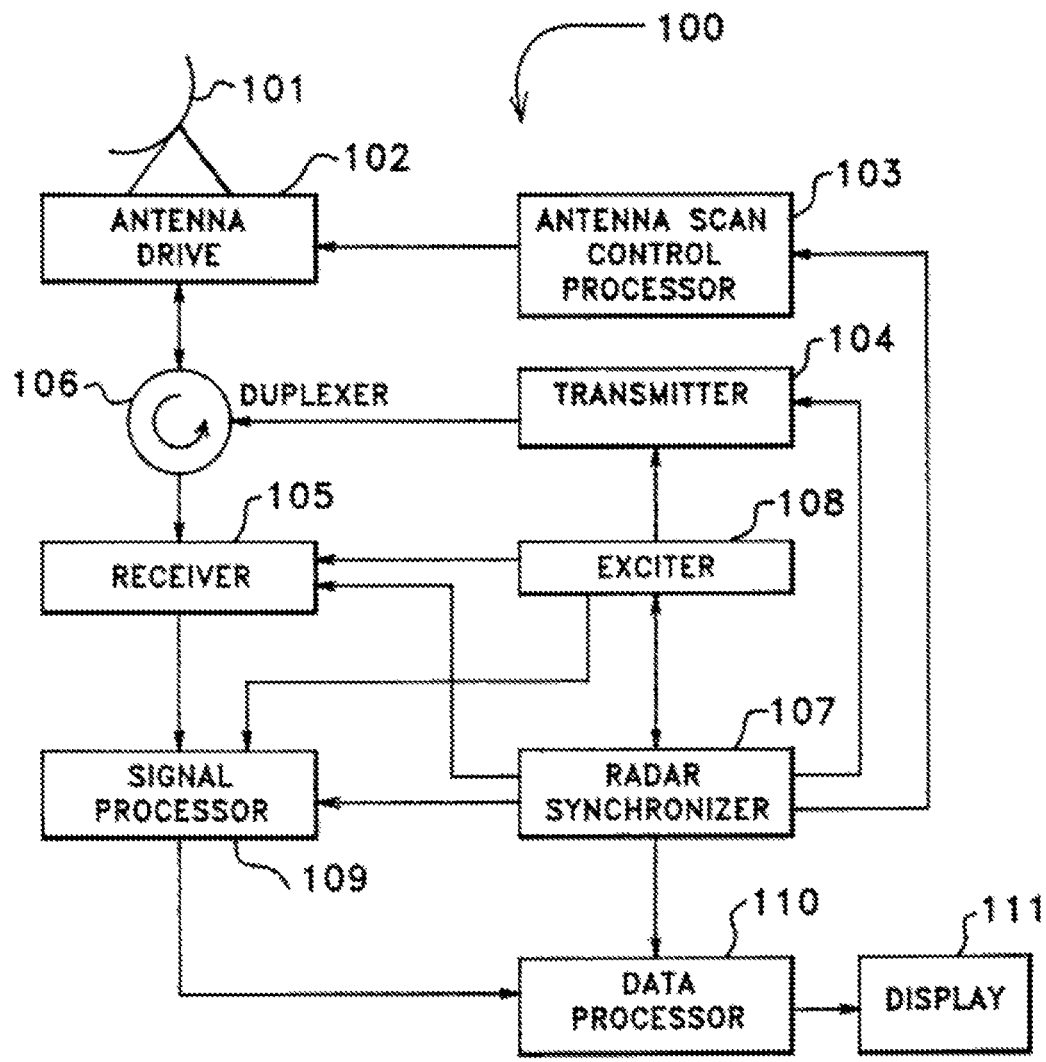
FIG. 2 is a functional block diagram of a typical Doppler radar system.

FIG. 2 is a functional block diagram of an exemplary prior art pulse Doppler weather radar system 100 used to detect meteorological events. The functional elements illustrated in FIG. 2 are well-known and are not disclosed in detail for simplicity and brevity of description. These elements are used to illustrate the underlying concepts of pulsed Doppler radar and may not exactly correspond to the physical entities found in a specific system. This pulsed Doppler radar system 100 consists of a directional antenna 101, such as a center feed circular parabolic reflector. The directional antenna 101 is mounted on a pedestal and can be moved through azimuth and elevation motions by drive motors 102 to scan a predetermined volume of space around the radar site. An antenna scan control processor 103 is used to regulate the servo systems that function to drive the azimuth and elevation drive motors 102 or to electronically steer the active antenna elements to guide the antenna beam through a scan pattern. A transmitter 104 and a receiver 105 are also included to couple signals through a duplexer 106 to the directional antenna 101 as is described in further detail below. A radar synchronizer 107 is used to control the operation of the various components of the Doppler radar system 100 and to provide the requisite synchronization therebetween. In particular, the radar synchronizer 107 transmits timing signals to the antenna scan control processor 103, transmitter 104 and receiver 105 as well as to an exciter 108, which generates the control signal waveforms used by the transmitter 104 and receiver 105 to produce a sequence of pulses of electromagnetic energy which constitute the pulsed Doppler radar signals.

The output of the exciter 108 consists of a series of output pulses which are applied to the transmitter 104. The transmitter 104 consists of an amplifier that increases the amplitude of the output pulses produced by exciter 108 to the desired level. The radio frequency signal is typically amplified by a high power amplifier, the output of which is fed to the directional antenna 101 through the duplexer 106. The directional antenna 101 provides an impedance match between the guided wave output of the radar transmitter 104 and the free space propagation of the radar pulse. The antenna characteristics determine the two-dimensional beam shape and beam width of the transmitted radar energy. The directional antenna 101 concentrates the transmitted energy into a particular solid angle, thereby amplifying the total radar energy in a particular direction as opposed to transmitting the radar energy equally in all directions. The pulse of radio frequency energy output by the directional antenna 101 travels through space until it hits a target, which acts as a reflector. The target intercepts a portion of the transmitted radar power and re-radiates it in various directions. A component of the re-radiated or reflected radar energy is detected by the directional antenna 101 and applied through the duplexer 106 to the receiver 105. The radar target, in reflecting the radar pulse, modifies the frequency of the transmitted radar waveform.

Weather surveillance radars continually scan a volume of space. The antenna beamwidth, antenna scan rate and pulse repetition frequency of such a radar determine the number of pulses transmitted per unit of time and hence the number of return echo signals received by the radar. A typical surveillance radar transmits a plurality of pulses during the time it takes the antenna beam to sweep across a target. Synchronization between the transmitter 104 and receiver 105 is necessary in order to accurately determine the correspondence between a transmitted pulse and its received reflected component to thereby determine the range of the target from the radar.

The reflected radar energy captured by the directional antenna 101 is sent to the radar receiver 105 via duplexer 106 which converts the frequency of the received energy (echo) from the radio frequency to an intermediate frequency. The receiver 104 amplifies the received echo signal and maximizes the signal to noise ratio of individual pulses. The resultant pulse information is sent to the signal processor 109, which interprets the content of the received echo signal. The signal processor 109 includes filters to minimize unwanted returns from clutter such as energy reflected by obstacles, topological features in the vicinity of the radar or other sources of unwanted noise. This signal processor 109 then presents its output to the data processor 110 which generates the customer useable output in the form of quality controlled data sets, a visual display, and/or alphanumeric displays to indicate the presence, locus and nature of targets detected in the radar beam scan pattern.

Target detection is performed in the radar receiver 105, signal processor 109, and data processor 110 subsystems. The radar receiver 105 must differentiate the reflected radar signal from the system noise background. The received signal strength depends on the target range and reflection characteristics of the target as well as the radar transmit power and antenna gain. As can be seen from FIG. 2, the radar system commonly transmits pulses of electromagnetic energy at a fixed rate called the pulse repetition frequency (PRF). The time interval between two successive pulses is called the pulse repetition interval (PRI). The pulse repetition interval is the reciprocal of the pulse repetition frequency. In operation, the radar synchronizer 108 and the exciter 107 operate to activate the transmitter 104 to produce a transmitted pulse of radio frequency energy at a predetermined time in the pulse repetition interval. A short time later, the synchronizer 107 enables the receiver's 105 signal reception to detect returning echo signals that represent reflected radar pulses from the present or a previously occurring pulse repetition interval. The receiver's signal reception is enabled for a predetermined duration during this pulse repetition interval in order to detect pulses of radio frequency energy reflected from a target within the scan of the antenna beam. The received echo signal represents the return echo from a transmitted pulse that occurred a certain number (p) of pulse repetition intervals prior to the presently occurring pulse repetition interval.

The data analyzed in the second example used for this study were from the 5 Jun. 2009 tornadic supercell in Goshen County, Wyoming and collected using the Doppler On Wheels (DOW) mobile Doppler radar system during the second Verification of the Origins of Rotation in Tornadoes Experiment (VORTEX2 (J. Wurman, et al., 2012, *Bull. Amer. Meteor. Soc.* 93 1147-1170; K. Kosiba, et al., 2013 *Mon. Wea. Rev.* 141 1157-1181).). Dual Doppler data from DOW 6 (Lat/Lon=−104.34732, 41.49556) and DOW7 (Lat/Lon=−103.25204, 41.61437) were combined in an objective analysis at 17 time points from 2142-2214 UTC equally spaced by 2 minute intervals on a Cartesian grid (centered at DOW6) of dimensions $\{nx, ny, nz\}=\{301, 301, 41\}$. The field of view in each dimension was $\{D_x, D_y, D_z\}=[100$ m, 100 m, 100 m]. The elevation angles (in degrees) used in the objective analysis for the two volumes were DOW6: $\{0.5, 1, 2, 3, 4, 5, 6, 8, 10, 12, 14, 16\}$; DOW 7: $\{1, 2, 3, 4, 5, 6, 0.5, 8, 10, 12, 14, 16\}$. Barnes analysis was used with $\kappa=0.216$ m² (horizontal=vertical). For the dual analysis, the minimum beam angle was $\phi_{min}=30°$. A 3-step Leise smoothing filter is applied to the vorticity, tilting, and stretching vectors and a one-step Leise filter to the velocity components (u, v, w). The mesocyclone movement was subtracted from the velocities (u, v).

The EFD analysis method can be applied to any one of the multitude of multidimensional parameters that characterize tornadic supercells. The analysis focuses on a few critical parameters: maximum radar reflectivity, vorticity, and vortex stretching. In particular, the focus is on the interplay of these parameter in relation to the descending reflectivity core (DRC), which has been implicated as a trigger mechanism in tornadogenesis. This approach is not meant to imply, of course, that these parameters are solely responsible for tornadogenesis, but rather to demonstrate the ability of the EFD analysis to detect the major modes of these (or other) parameters that are of particular interest.

Figure 8:
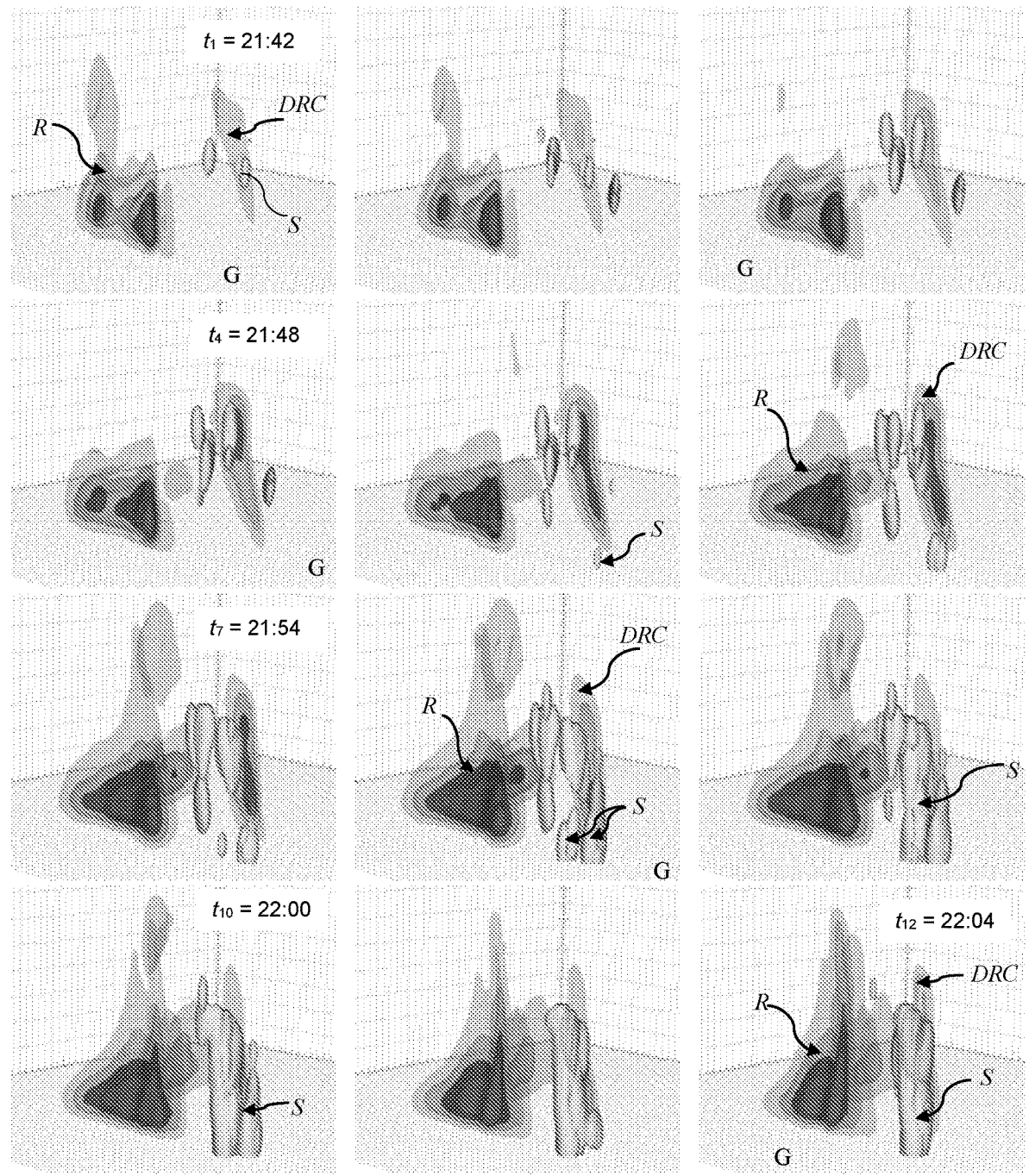
FIG. 8 is a series of twelve time frames following EFS analysis of mobile Doppler radar data.

The spatial-temporal modes are analyzed for the first twelve time frames of the data, from $t_1=21:42$ until $t_{12}=22:04$, in equal time steps of $\Delta t=00:02$ min. The time development of the major spatio-temporal modes of maximum reflectivity and stretch derived from EFD analysis are shown in FIG. 8. The reflectivity R is displayed with multiple (3) different colored contour levels in order to highlight the development of the structure of the descending reflectivity core (DRC), while the stretch is displayed as a single contour S. The reflectivity R is contoured on a linear scale while the stretch S is contoured on a log scale. The area of heaviest precipitation is seen on the left with the rfmax contours at or near ground level. The DRC is evident but weak at the initial frame ($t_1=21:42$) where it appears as a finger on the right side of the plot adjacent to a few small regions of increased stretch S. Subsequent time frames show increasing reflectivity and the descent of the core towards the ground G along with an increase in the stretch. At $t_5=21:50$, the first significant contour of stretch S touching the ground G is observed near the tip of the lowest level of the DRC. At $t_7=21:54$, a second region of stretch near the ground emerges just southwest of the stretch at the base of the DRC. At the same time, two adjacent stretch contours aloft, and nearly the same vertical extent of the DRC, are seen to coalesce at approximately above the two stretch regions on the ground. By $t_8=21:56$, there are two prominent stretch contours on ground, in contact with and infiltrating the DRC, as stretch contours aloft appear to dissipate. At $t_9=21:58$, this coalescence has resulted in a prominent stretch contour S nearly coincident with the DRC and an adjacent stretch contour which continues to grow and merge with the larger stretch contour S, until $t_{12}=22:04$, when complete coalescence has taken place.

Figure 9:
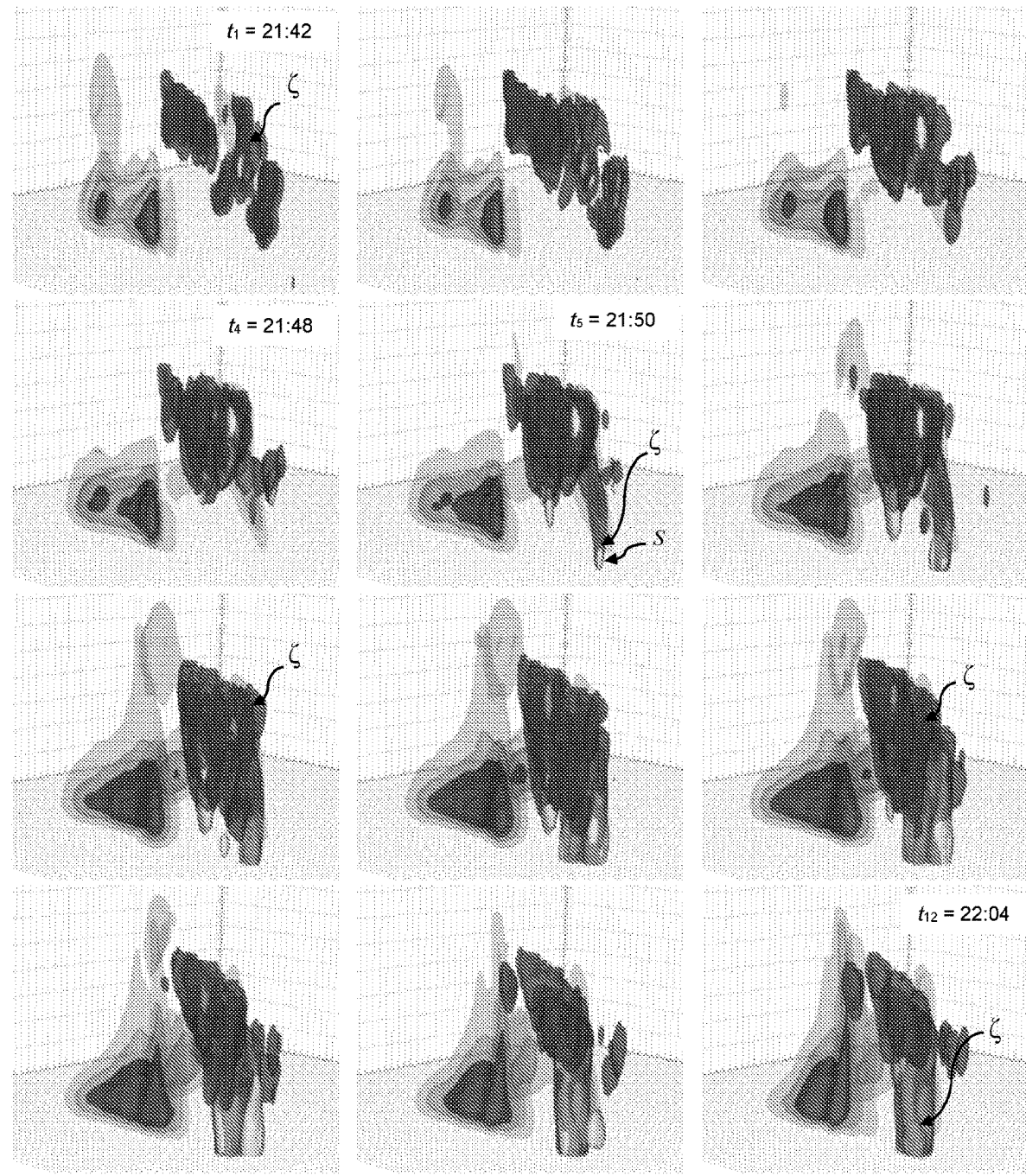
FIG. 9 is the series of twelve time frames following EFS analysis of mobile Doppler radar data shown in FIG. 8 with added EFD-estimated vorticity.

The same results of FIG. 8 are shown along with the EFD estimated vorticity in FIG. 9. The vorticity contours $\zeta$ like the stretch contours S, are shown in a single color and for a single value. The contours were generated on a linear scale. These results confirm what one would expect from the fact that increasing stretch increases vorticity, as the vorticity contours surround the stretch contours. As the stretch contours S coalesce and descend with the DRC, so do the vorticity contours $\zeta$ Vorticity at low elevations is seen in frames $t_1$ through $t_4$ and appears to first touch the ground at $t_5$, when the first ground based stretch contour appears. The evolving stretch con-tours closest to the DRC that extend up from the ground level produce evolving, increasing, and localized vorticity through the last time step $t_{12}$.

Figure 10:
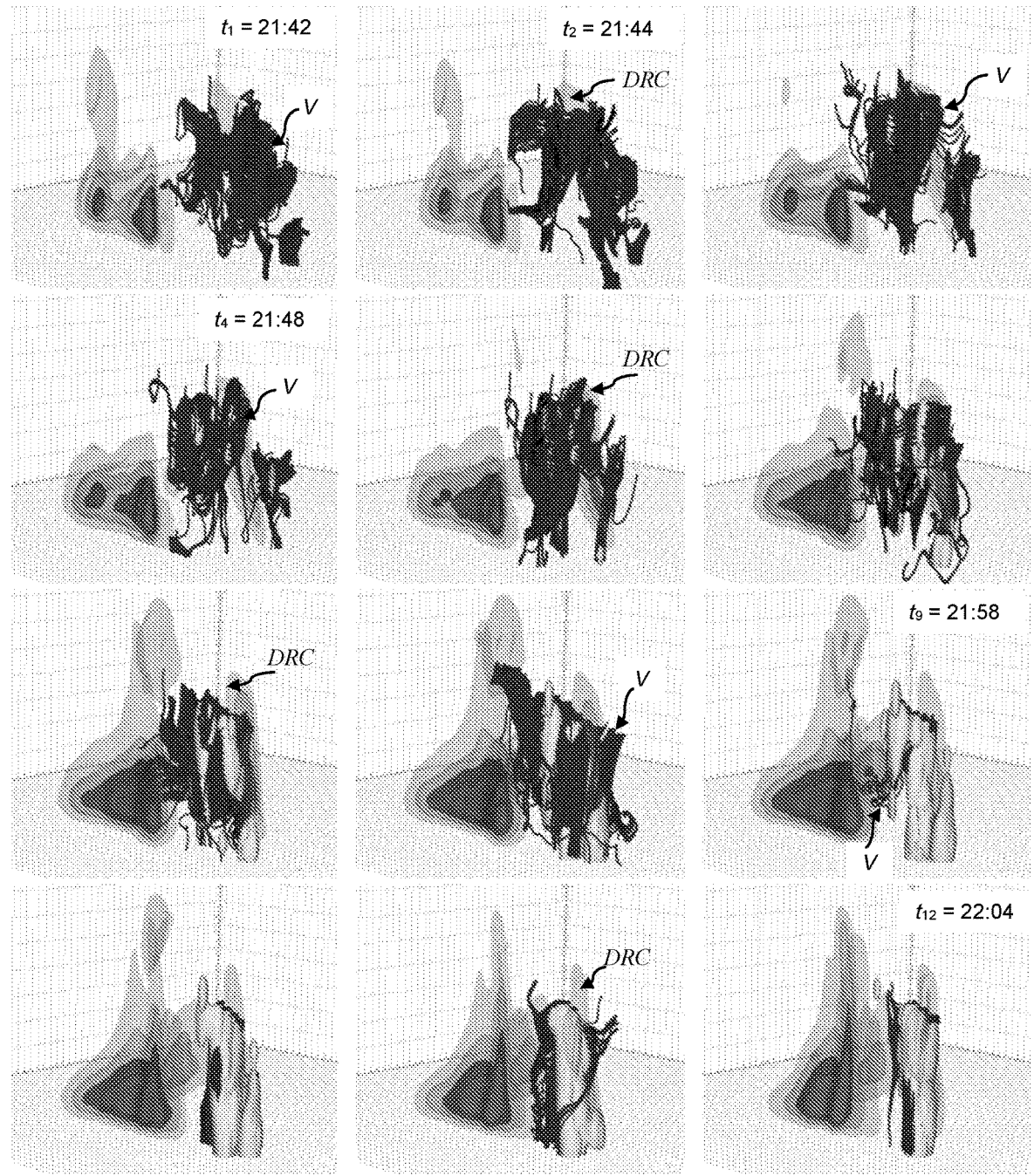
FIG. 10 is the series of twelve time frames following EFS analysis of mobile Doppler radar data shown in FIG. 8 with EFD-generated vortex line tracts.
Figure 11:
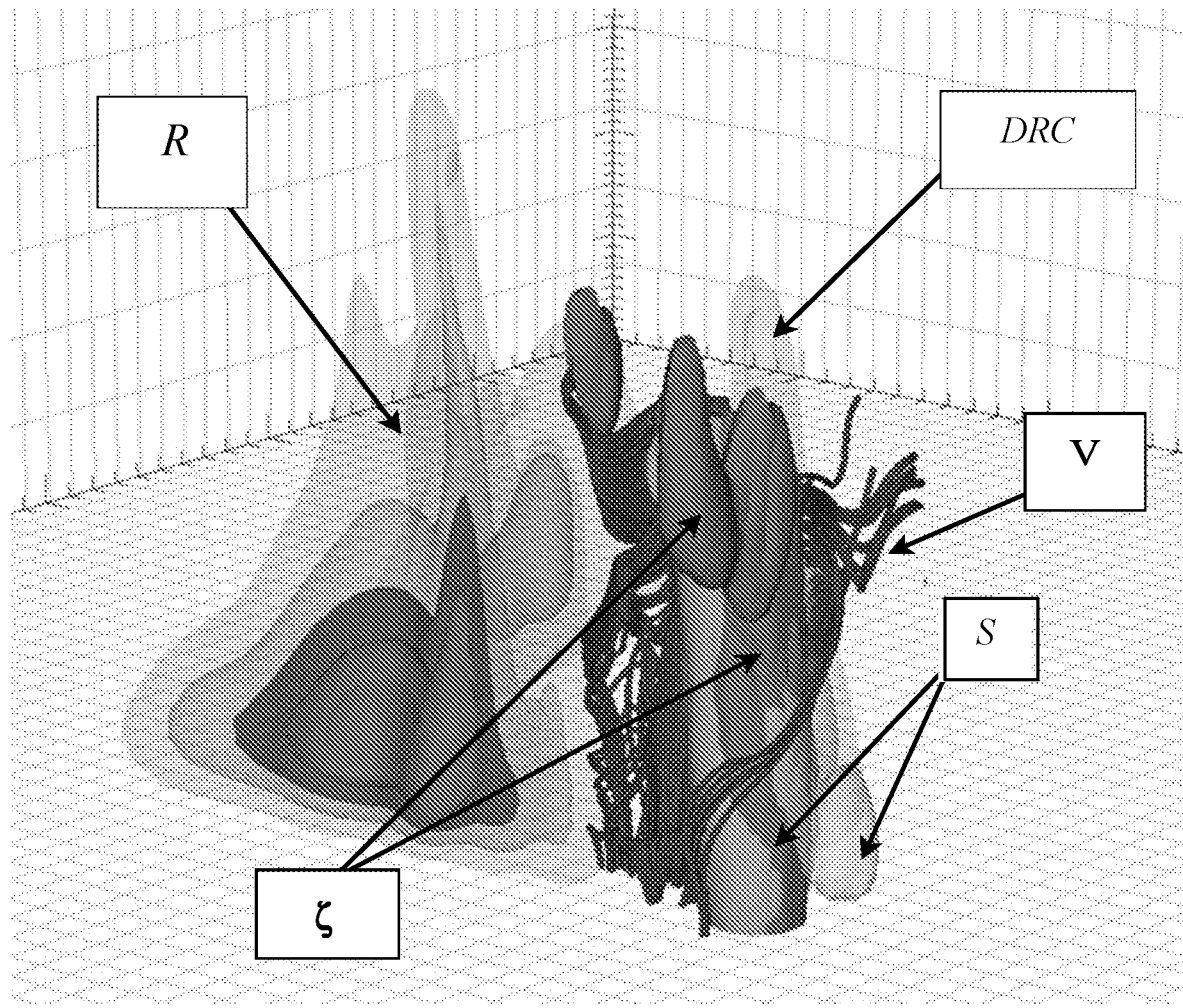
FIG. 11 shows the results of EFS analysis of mobile Doppler radar data with EFD-estimated vorticity and EFD-generated vortex line tracts.

The same results of FIG. 8 are shown along with the EFD generated vortex line tracts in FIG. 10. The stretch contour surfaces were used as seed points for generating the tracts, as it is these surfaces that are expected to enhance local vorticity. Of particular interest is the evolution of vortex lines at times $t_2$-$t_4$ which appear to extend from the base of the DRC at $t_2$ above the ground to touching the ground at $t_3$. In frames $t_2$-$t_4$, these vortex lines are clearly seen to be aligned along the DRC, which appears to have a focusing effects, the bundle of vortex lines tight-ens at the same time it reaches the ground. At $t_5$ there is a clear vertical vortex bundle co-localized with the primary ground-base stretch contour. Throughout all the frames, near ground looping vortex lines V are apparent, consistent with the "vortex arches" that have been detected by traditional means ((Markowski et al. 2012a)). However, the vortex bundles near the base of the DRC are the primary ones that appear to organize and tighten near the ground as they coalesce with the primary stretch contours, with which they are nearly coincident by $t_9$.

Referring to FIG. 10, modes of reflectivity R (contours 810), vertical vorticity $\zeta$ 820, the stretching S of vertical vorticity from a single time step are shown along with vorticity tracts V 830 generated by functional tractography. The generation and intensification of low-level rotation is clearly detected in the major modes detected by EFD, and appears to be consistent with recent theories focusing on the role of the descending reflectivity core (DRC) 840. Aside from the initial data preparation described by Wurman et al. and Kosiba, et al., no processing other than the EFD algorithm described above was used. In particular, no noise filtering of any kind was employed.

Understanding the mechanisms of tornado formation has long been a focus of the severe weather research community. However, the extreme complexity of tornadic events precludes a satisfactory analytical approach and, while numerical simulations are a promising approach that shows increasingly realistic results, they currently remain incapable of capturing the complete complexity of actual tornadic events. The analysis of observational data therefore remains the primary source of information regarding tornadogenesis. Of course the obvious major benefit of the capability of deriving tornadic signatures in real data is the possibility that they may be used to forecast events in near real time and be used to enhance public warning systems.

However, current analysis method in severe weather meteorology rely on essentially qualitative methods based on standard graphics methods such as isosurface rendering of calculated parameters. Mobile Doppler radar systems, such as the DOW program have made dramatic improvements in the accuracy, stability, and resolution of their systems, resulting in ever increasing quality of the spatio-temporal data in tornadic storms. The problem then rests on the ability to accurately and robustly analyze spatio-temporal phenomenon in time resolved volumetric multivariate and noisy data sets. The difficulties in formulating a quantitative approach to this problem are not unique to severe weather meteorology, but appear in other fields of image or multivariate data analysis as well.

In the context of mobile Doppler radar data, the EFD approach allows coupling to be defined in terms of parameters resulting from the standard objective analysis, giving a flexibility to use scalar or vector (or even multiscale tensor) coupling. Using the general analysis discussed herein produces ranked modes of the storm that clearly reveal the spatial temporal modes of the critical variables in tornadogenesis, such as tilt, stretch and vorticity. The generation and intensification of low-level rotation is readily apparent in the major modes detected by EFD, and appears to be consistent with recent theories focusing on the role of the descending reflectivity core. This core, and the convergence, intensification, and coalescence of the vorticity as mediated by the tilt and stretch are automatically detected and quantified using the EFD method, providing new insight into the quantitative dynamics of tornadogenesis, while offering the possibility of an analysis system capable of being used in conjunction with severe weather radar instrumentation to develop early warning systems.

Application of the EFD method to analysis of weather data will enable commercial development of a severe weather detection and warning system. The EFD method offers the possibility of an automated detection of severe weather events and thus a much more efficient means of processing Doppler radar data. It facilitates the use of a larger networks of detection devices, such as could be designed using the new technology of flexible, easily installed transmitters and antennae built from electromagnetic metamaterials. Such instrumentation could be used as Doppler transmitting and receiving antenna, installed in a region where severe weather is a common hazard (e.g., Kansas and Oklahoma) on virtually any outdoor structure (such as a grain silo) located preferentially out in the open and high enough to "see" over most buildings. Using such low cost and easily installed hardware in conjunction with our novel detection software, a vast and dense network of severe weather radar stations could be set up to significantly reduce the risk to a large population of people.

Example 5: Root Phenotyping

Another application of the methods described herein is the non-invasive quantitation of root architecture including basic parameters such as depth and maximum angular extent, but also additional characterization in terms of angular distributions and network properties. The method is non-invasive and thus can be used in longitudinal studies without disrupting the plant system.

The application of ESP and EFD to evaluation of root structure is unique in two distinct aspects. First, the application of diffusion weighted MRI in this context is novel and provides significant advantages over traditional root measurement methods, which are either invasive and based on simple photographic methods, or are based on 3D anatomical imaging methods (anatomical CT or MRI) that are not able to quantitate local water transport properties. Second, the DT-MRI analysis is unique amongst all existing DTI methods in its ability to accurately quantitate complex intertwining pathways containing water diffusion. Together, these characteristics provide a unique method for the non-invasive quantitation of both local water transport within a complex root system network as well as quantitation of the global network structure derived from these local measurements. The simultaneous estimation of both these local and global properties provide the basis for characterization of a root system in terms of a both its water transport properties and its global structure.

The inventive method is superior to existing methods, which are either visual inspection ("shovelomics") or 3D anatomical imaging (CT or MRI). The first is only qualitative, while the latter only provide 3D visualizations of root systems, without any physiological information. Further, they do not provide a method for constructing root pathways that lead to a characterization of root networks.

According to an exemplary embodiment, a standard MR imaging system is used to acquire diffusion weighted MRI data of a living root system with multiple b-values, with equi-angular sampling at each b-value. Lower b-values require fewer angular samples. The data are then processed using the GO-ESP algorithm as described and in the related application incorporated herein by reference (U.S. Patent Publication No. US2016/0110911) and the spherical wave decompositions (SWD) described in International Publication No. WO2015/039054, which is incorporated herein by reference. This analysis provides a quantitative measure of the 3D distribution of the local diffusion (water transport) in the 3D root system. The fiber tracts generated by the GO-ESP algorithm provide the pathways of the individual root branches and thus can be used to identify in automated manner different root systems (primary, lateral, seminal, etc.) and to derive quantitative geometric measures (angle distributions, amount of branching) as well as network properties (connectivity, fractal dimensions, etc.)

Commercial applications of the ESP and EFD methods include development of plant phenotypes for use in drought-stricken regions of the world, and development of plants optimized to grow in specified soil types.

Figure 12:
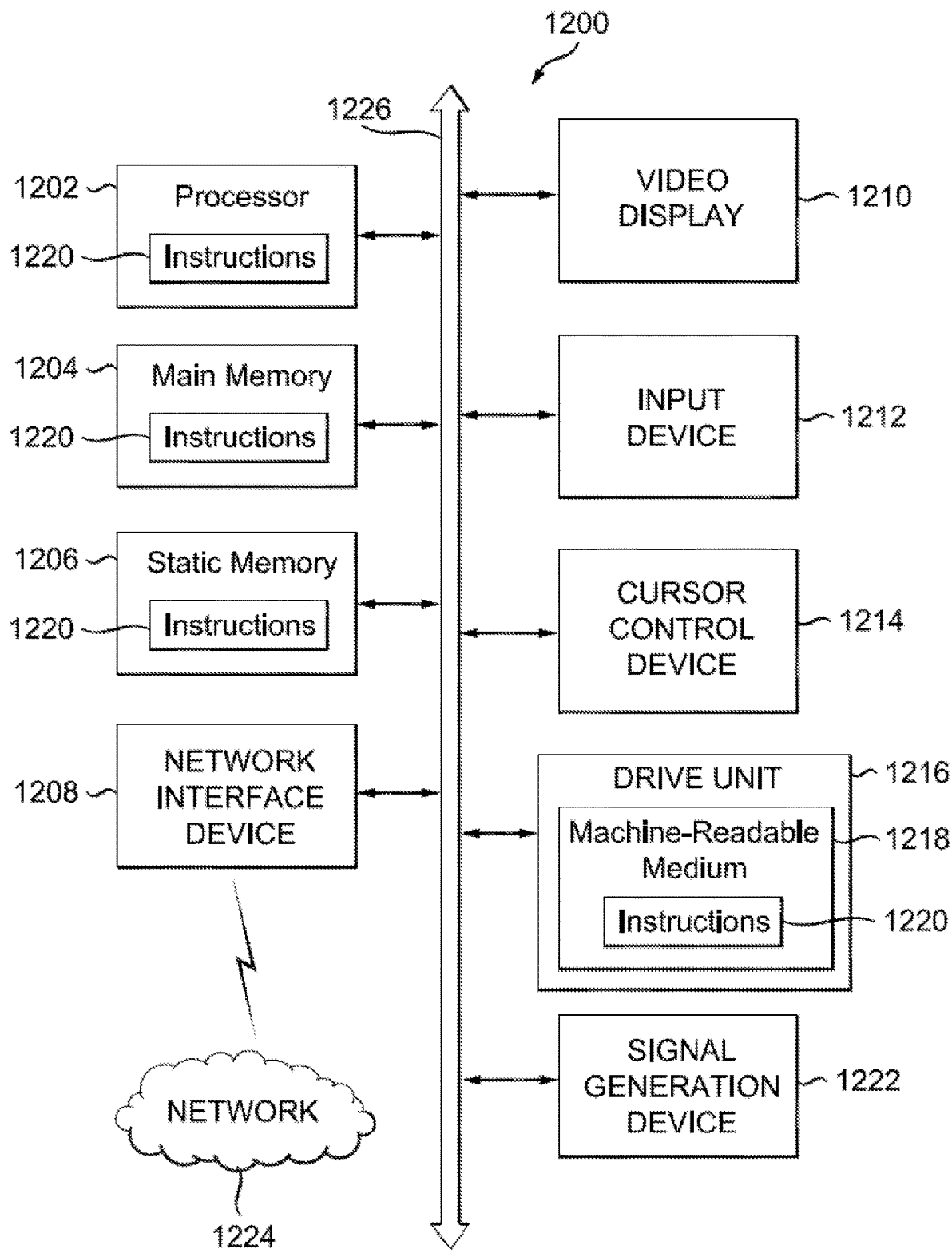
FIG. 12 is a block diagram of an embodiment of a general computer system that may be used for implementation of the EFD method.

FIG. 12 is a block diagram of an illustrative embodiment of a general computer system 1200. The computer system 1200 can be the computer 226 of FIG. 1 or the data processor 110 of FIG. 2. The computer system 1200 can include a set of instructions that can be executed to cause the computer system 1200 to perform any one or more of the methods or computer based functions disclosed herein. The computer system 1200, or any portion thereof, may operate as a standalone device or may be connected, e.g., using a network or other connection, to other computer systems or peripheral devices.

The computer system 1200 may also be implemented as or incorporated into various devices, such as a personal computer (PC), a tablet PC, a personal digital assistant (PDA), a mobile device, a palmtop computer, a laptop computer, a desktop computer, a communications device, a control system, a web appliance, or any other machine capable of executing a set of instructions (sequentially or otherwise) that specify actions to be taken by that machine. Further, while a single computer system 1200 is illustrated, the term "system" shall also be taken to include any collection of systems or sub-systems that individually or jointly execute a set, or multiple sets, of instructions to perform one or more computer functions.

The computer system 1200 may include a processor 1202, e.g., a central processing unit (CPU), a graphics-processing unit (GPU), or both. Further, the computer system 1200 may include a main memory 1204 and a static memory 1206, which can communicate with each other via a bus 1226. As shown, the computer system 1200 may further include a video display unit 1210, such as a liquid crystal display (LCD), a light emitting diode (LED), a flat panel display, a solid state display, or a cathode ray tube (CRT). Additionally, the computer system 1200 may include an input device 1212, such as a keyboard, and a cursor control device 1214, such as a mouse or trackpad. The computer system 1200 may also include a disk drive unit 1216 or other peripheral memory device, a signal generation device 1222, such as a speaker or remote control, and a network interface device 1208.

In some embodiments, as depicted in FIG. 12, the disk drive unit 1216 may include a computer-readable medium 1218 in which one or more sets of instructions 1220, e.g., software, can be embedded. Further, the instructions 1220 may embody one or more of the methods or logic as described herein. In some embodiments, the instructions 1220 may reside completely, or at least partially, within the main memory 1204, the static memory 1206, and/or within the processor 1202 during execution by the computer system 1200. The main memory 1204 and the processor 1202 also may include computer-readable media.

The method of entropy field decomposition (EFD), which combines structural analysis techniques, entropy spectrum pathways (ESP), and IFT is useful for the analysis and quantitation of a variety of spatio-temporal patterns. The specific examples of application to analysis of FMRI data, Doppler radar data, and plant phenotyping described herein are illustrative and are not intended to be limiting. The overall EFD method is, in fact, applicable to any field that would benefit from improved analysis of complex spatio-temporal patterns.

REFERENCES (INCORPORATED HEREIN BY REFERENCE)

[1] Smith, S. M., et al., 2013 *Neuroimage* (80) 144-168.
[2] Heine L., et al., 2012 *Frontiers in Psychology* (3) 1-12.
[3] Wurman J. M., et al., 2010 *Mon. Wea. Rev.* (138) 4439-4455.
[4] Marquis J., et al., 2012 *Mon. Wea. Rev.* (140) 3-27.
[5] Kosiba K., et al., 2013 *Weather Forecast.* (28) 1552-1561.
[6] Christakos G., 1991 *IEEE Transactions on Systems, Man and Cybernetics*, (21) 861-875.
[7] Broomhead D., et al., 1987 *Physica D* (20) 217-236.
[8] Spencer K, et al., 2001 *Psychophysiology* (38) 343-358
[9] Bell A., et al., 1995 *Neural Comput* (7) 1129-1159.
[10] Hyvarinen A., et al., 2000 *Neural Networks* (13) 411-430.
[11] Ghil M., et al., 2002 *Reviews of Geophysics* (40).
[12] Wallace J. M., et al., 1992 *Journal of Climate* (5) 561-576.
[13] Plaut G., et al., 1994 *J. Atmos. Sci.* (51) 210-236.
[14] Dixon M., et al., 1993 *J. Atmos. and Oceanic Tech.* (10) 785-797.
[15] Min W., et al. 2011 *Transportation Research Part C-Emerging Technologies* (19) 606-616.
[16] Hill M. J., et al., 2003 *Remote Sensing of Environment* (84) 367-384.
[17] Gallez D., et al., 1991 *Biological Cybernetics* (64) 381-391.
[18] Bijma F., et al., 2005 *NeuroImage* (27) 402-415.
[19] Plis S., et al., 2007 *Physical Review* E (75) 011928.
[20] Lamus C., et al., 2012 *NeuroImage* (63) 894-909.
[21] McKeown M. J., et al., 1998 *Science* (6) 160-188.
[22] Calhoun V. D., 2001 *Human Brain Mapping* (13) 43-53.
[23] Kiviniemi V., et al., 2003 *Neuroimage* (19) 253-260.
[24] Beckmann C. F., et al., 2004 *IEEE Trans. Med. Imaging* (23) 137-152.
[25] Tian L., et al, 2013 *PLoS ONE* (8) 1-12.
[26] Uhl C., et al., 1993 *Zeitschrift für Physik B Condensed Matter* (92) 211-219.
[27] Uhl C., et al., 1995 *Physical Review E* (51) 3890-3900.
[28] Jaynes E., 2003 *Probability Theory: The Logic of Science* (New York: Cambridge University Press).
[29] Enßlin T. A., et al., 2009 *Phys Rev D* (80) 105005.
[30] Frank L. R., et al., 2014 *Phys. Rev. E* 89(3) 032142.
[31] Smith S. M., et al., 2013 *NeuroImage* (80) 144-168.
[32] Haimovici A., et al., 2013 *Phys. Rev. Lett.* 110(17) 178101.
[33] Smith S. M., et al, 2009 *Proc. Nat. Acad. of Sci.* (106) 13040-13045.
[34] Zalesky A., et al., 2014 *Proc. Nat. Acad. of Sci.* (111) 10341-10346.
[35] Wurman J., et al., 1997 *J. Atmos. Oceanic Technol.* (14) 1502-1512.
[36] Wurman J., et al., 2012 *Bull. Amer. Meteor. Soc.* (93) 11471170.
[37] Kosiba K., et al., 2013 *Mon. Wea. Rev.* (141) 1157-1181.
[38] Jaynes E., 1974 *Probability Theory with Applications in Science and Engineering* (Washington University; Fragmentary ed edition).
[39] Chaichian M., 2001 *Path Integrals in Physics: Volume II Quantum Field Theory, Statistical Physics and other Modern Applications Institute of physics series in mathematical and computational physics* (Taylor & Francis) ISBN 9780750308021.
[40] Tan S. M., 1986 *Monthly Notices of the Royal Astronomical Society* (220) 971-1001
[41] Burda Z, et al., 2009 *Phys. Rev. Lett.* (102) 160602.
[42] Burda Z., et al., 2010 The Various Facets of Random Walk Entropy, *Acta Physica Polonica B* (Jagellonian Univ, Marian Smoluchowski Inst Phys, PL-30059 Krakow, Poland) pp 949-987.
[43] Burda Z., et al 2010 *Arxiv preprint arXiv:* 1004.3667.
[44] Jaynes E., 1957 *Physical Review* (106) 620-630.
[45] Jaynes E., 1957 *Physical Review* (108) 171.
[46] Buxton R., et al., 1997 *J. Cerebr. Blood F Met* (17) 64-72.
[47] Buxton R. B., et al., 1998 *Magn. Reson. Med.* (39) 855-864.
[48] Buxton R., et al., 2004 *Neuroimage* (23) S220-S233.
[49] Logothetis N. K., et al., 2001 *Nature* (412) 150-157.
[50] Bullmore E., 1996 *Magn. Reson. Med.* (35) 261-277, ISSN 1522-2594.
[51] Wong C. W., et al., 2013 *Neuroimage* (83) 983-990.
[52] Markowski P. M., et al. 2009 *Atmos. Res.* (93) 3-10.
[53] Markowski P., et al., 2012 *Mon. Wea. Rev.* (140) 2887-2915.
[54] Markowski P., et al., 2012 *Mon. Wea. Rev.* (140) 2916-2938.
[55] von Storch H., et al., 2001 *Statistical Analysis in Climate Research* (Cambridge University Press) ISBN 9780521012300.
[56] Jazwinski A., 1970 *Stochastic Processes and Filtering Theory Mathematics in Science and Engineering* (Elsevier Science) ISBN 9780080960906.
[57] Comon P., 1994 *Signal Process* (36) 287-314.
[58] Beckmann C. F., et al., 2005 *Philos T Roy Soc B* (360) 1001-1013.
[59] Tipping M. E., et al., 1999 *Neural Computation* (11) 443-482.
[60] Varoquaux G., et al., 2010 *Neuroimage* (51) 288-299.
[61] Barnes S. L., 1964 *J. Appl. Meteorol.* (3) 396-409.
[62] Leise J. A., 1982 *NOAA Tech. Memo.* ERL WPL-82.

The invention claimed is:

1. A method for analysis of complex spatio-temporal data, the method comprising, in a computer processor:
receiving image data from an image detector, wherein the image data comprises points within a lattice;
ranking a plurality of optimal paths within the lattice according to path entropy, wherein the rankings are arranged in a coupling matrix;
using eigenvalues and eigenvectors from the coupling matrix to construct an information Hamiltonian;
determining mode amplitudes corresponding to spatially and temporally interacting modes of the information Hamiltonian; and
generating an output comprising a display of the mode amplitudes.

2. The method of claim 1, wherein the information Hamiltonian is of the form $$H(d, a_k) = -j_k^\dagger a_k + \frac{1}{2}a_k^\dagger \Lambda a_k + \sum_{n=1}^{\infty}\frac{1}{n!}\sum_{k_1}^{K}\cdots\sum_{k_n}^{K}\tilde{\Lambda}_{k_1\ldots k_n}^{(n)}a_{k_1}\cdots a_{k_n},$$

where matrix $\Lambda$ is the diagonal matrix $\text{Diag}\{\lambda_1, \ldots, \lambda_K\}$ composed of eigenvalues of a noise corrected coupling matrix, $a_k$ is an amplitude of the kth mode, and $j_k$ is the amplitude of the kth mode in the expansion of the source j.

3. The method of claim 2, wherein the mode amplitudes are determined according to the relationship $$\Lambda a_k = \left(j_k - \sum_{n=1}^{\infty}\frac{1}{n!}\sum_{k_1}^{K}\cdots\sum_{k_n}^{K}\tilde{\Lambda}_{kk_1\ldots k_n}^{(n+1)}a_{k_1}\cdots a_{k_n}\right).$$

4. The method of claim 1, wherein the image detector comprises a magnetic resonance imaging system and the complex spatio-temporal data comprises functional magnetic resonance image (FMRI) data, and wherein the mode amplitudes correspond to functional tractography and functional eigentracts.

5. The method of claim 1, wherein the image detector comprises a Doppler radar system and the complex spatio-temporal data comprises Doppler radar data, and wherein the mode amplitudes correspond to tilt, stretch and vorticity.

6. A method for analysis of complex multivariate spatio-temporal data, comprising:
   receiving in a computer processor image data from an image detector, wherein the image data comprises a plurality of voxels; and
   causing the computer processor to perform the steps of:
      ranking pathways between voxels according to path entropy and generating a coupling matrix therefrom;
      determining eigenvalues and eigenvectors for the coupling matrix;
      constructing an information Hamiltonian using eigenvalues and eigenvectors;
      determining mode amplitudes corresponding to spatially and temporally interacting modes of the information Hamiltonian; and
      generating an output comprising a display of the mode amplitudes.

7. The method of claim 6, wherein the information Hamiltonian is of the form $$H(d, a_k) = -j_k^\dagger a_k + \frac{1}{2}a_k^\dagger \Lambda a_k + \sum_{n=1}^{\infty}\frac{1}{n!}\sum_{k_1}^{K}\cdots\sum_{k_n}^{K}\tilde{\Lambda}_{k_1\ldots k_n}^{(n)}a_{k_1}\cdots a_{k_n},$$

where matrix $\Lambda$ is the diagonal matrix $\text{Diag}\{\lambda_1, \ldots, \lambda_K\}$ composed of eigenvalues of a noise corrected coupling matrix, $a_k$ is an amplitude of the kth mode, and $j_k$ is the amplitude of the kth mode in the expansion of the source j.

8. The method of claim 6, wherein the mode amplitudes are determined according to the relationship $$\Lambda a_k = \left(j_k - \sum_{n=1}^{\infty}\frac{1}{n!}\sum_{k_1}^{K}\cdots\sum_{k_n}^{K}\tilde{\Lambda}_{kk_1\ldots k_n}^{(n+1)}a_{k_1}\cdots a_{k_n}\right).$$

9. The method of claim 6, wherein the image detector comprises a magnetic resonance imaging system and the complex spatio-temporal data comprises functional magnetic resonance image (FMRI) data, and wherein the mode amplitudes correspond to functional tractography and functional eigentracts.

10. The method of claim 6, wherein the image detector comprises a Doppler radar system and the complex spatio-temporal data comprises Doppler radar data, and wherein the mode amplitudes correspond to tilt, stretch and vorticity.

* * * * *